United States Patent [19]
Endo et al.

[11] Patent Number: 5,934,805
[45] Date of Patent: Aug. 10, 1999

[54] METHOD AND AN APPARATUS FOR FLAW DETECTION

[75] Inventors: Toshio Endo; Tomikazu Yagi, both of Aichi-ken; Ryuzo Yamada; Nobuo Ishikawa, both of Chita; Taizo Yano, Nagoya, all of Japan

[73] Assignee: Daido Tokushuko Kabushika Kaisha, Nagoya, Japan

[21] Appl. No.: 08/807,459

[22] Filed: Feb. 27, 1997

Related U.S. Application Data

[63] Continuation-in-part of application No. 08/242,953, May 16, 1994, abandoned.

[30] Foreign Application Priority Data

May 17, 1993 [JP] Japan ................................. 5-139337
Nov. 8, 1993 [JP] Japan ................................. 5-303430

[51] Int. Cl.⁶ .............................. G01J 5/00; G01N 25/72
[52] U.S. Cl. .............................. 374/5; 374/121; 374/126
[58] Field of Search ............................ 374/4, 5, 120, 374/121, 124, 126, 137; 219/667, 672, 674; 427/458, 466, 469, 472, 474

[56] References Cited

U.S. PATENT DOCUMENTS

| | | | |
|---|---|---|---|
| 3,020,745 | 2/1962 | Sielicki | 374/5 |
| 3,504,524 | 4/1970 | Maley | 375/5 |
| 4,247,306 | 1/1981 | Berge | 374/5 |
| 4,317,978 | 3/1982 | Nebesar | 219/667 |
| 4,408,903 | 10/1983 | Baldasarri | 374/126 |
| 4,430,913 | 2/1984 | Williamson | 82/70.2 |
| 4,480,928 | 11/1984 | Halsor et al. | 374/5 |
| 4,965,451 | 10/1990 | Solter | 374/4 |
| 5,069,005 | 12/1991 | Hovland et al. | 374/5 |
| 5,111,048 | 5/1992 | Devitt et al. | 374/5 |

FOREIGN PATENT DOCUMENTS

| | | | |
|---|---|---|---|
| 54-143184 | 11/1979 | Japan | 374/126 |
| 2109927 | 6/1983 | United Kingdom . | |

*Primary Examiner*—Diego Gutierrez
*Assistant Examiner*—Andrew Hirshfeld
*Attorney, Agent, or Firm*—Ronald R. Snider

[57] ABSTRACT

The surface of the member to be inspected is covered with powder deposited by using, for example, static electricity prior to the flaw detection. The member surface is covered so as to be partly exposed by setting the average thickness of the powder layer to 0.1D–0.6D, where D is the average particle diameter of the powder, under an assumption that the powder particles in the powder layer are virtually leveled into a uniform thickness film. Subsequently, the surface region of the member is heated by high frequency induction heating, and then the temperature distribution on the surface is measured with a radiation thermometer. The part for which the temperature measured is different from the surroundings is judged as a flaw. The surface of the member is covered with the powder so that the surface emissivity becomes almost uniform, and the resulting temperature distribution measured with the radiation thermometer becomes almost equal to the real one. Therefore, flaws existing on the surface of the member are precisely detected according to the measurement with the radiation thermometer even in the case that there are parts of low emissivity, such as handling marks, on the surface.

15 Claims, 25 Drawing Sheets

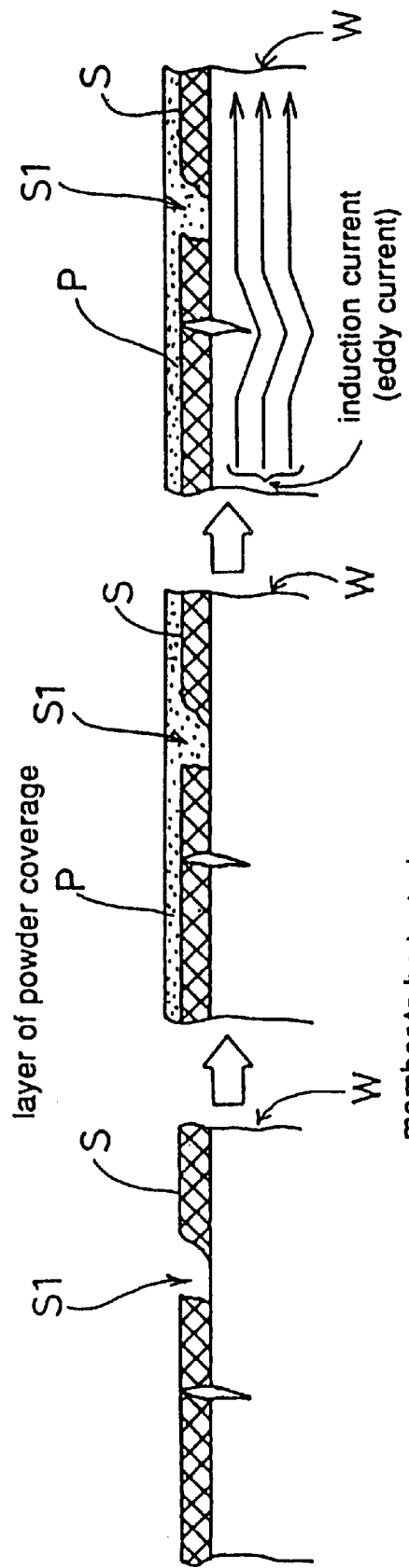

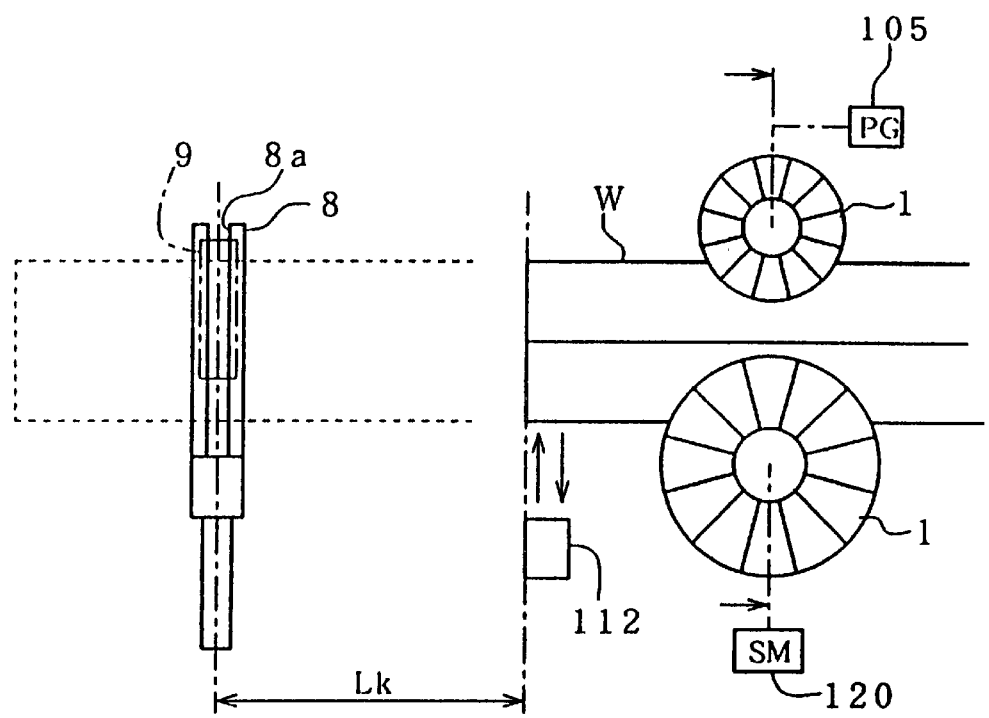
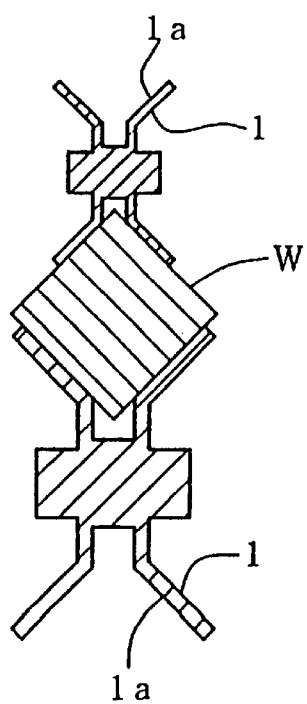
FIG.16

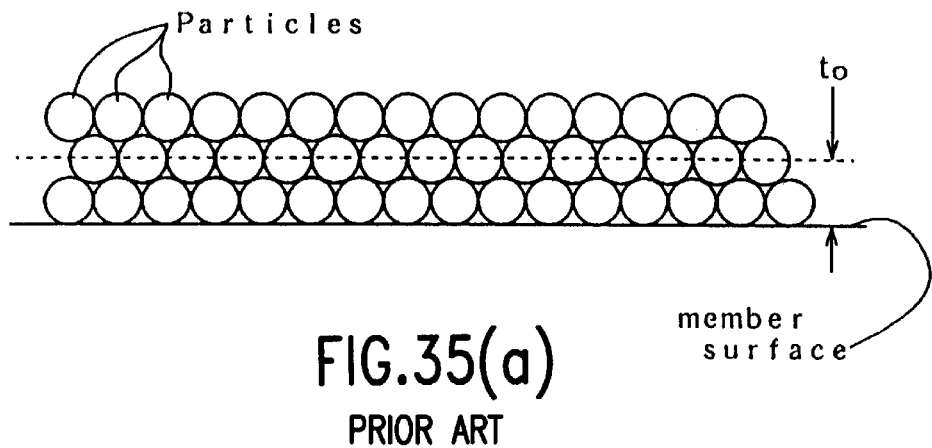
FIG.35(a)
PRIOR ART
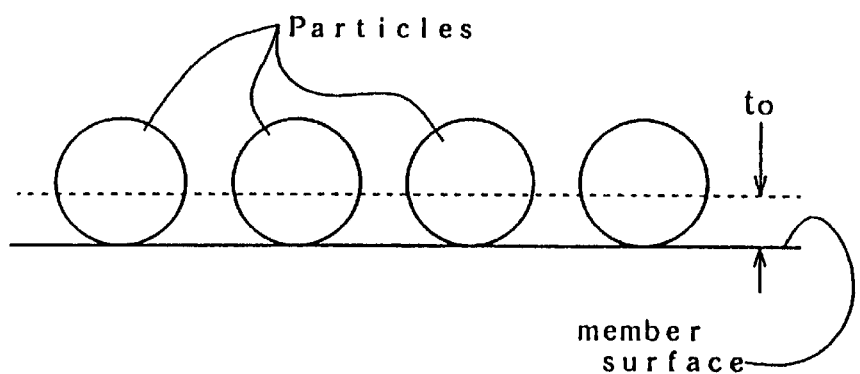
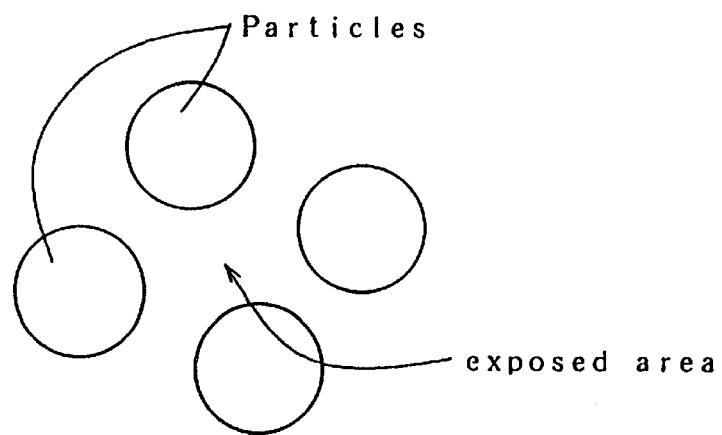
FIG.35(b)

METHOD AND AN APPARATUS FOR FLAW DETECTION

This application is a continuation-in-part and claims the priority of U.S. patent application Ser. No. 08/242,953, filed May 16, 1994, which is now abandoned.

FIELD OF INVENTION

This invention relates to a method and an apparatus for detecting flaws existing on a member to be inspected such as a steel member.

BACKGROUND OF THE INVENTION

For detecting flaws (including cracks) existing on a steel member, there is a known technique wherein the surface region of the member is heated by high frequency induction heating, and the flaws on the surface of the member are detected by measuring the surface temperature of the member with a radiation thermometer. This technique is disclosed in Japanese Provisional Publication No. 298846/90 and in corresponding U.S. Pat. No. 5,069,005. As shown more specifically in FIG. 36, the surface region of the member W to be inspected is heated by using a high frequency induction heating coil 8 during transportation, and then the temperature distribution on the surface of the member W is measured with a radiation thermometer 9 arranged just next to the coil 8. If a flaw exists on the surface, the temperature at the flaw is different from the sound part (higher or lower than the surroundings, for example) so that the flaw is detected according to this temperature difference.

Although a member covered with scale can be adopted for the flaw detection mentioned above, the member is treated by shot blasting as a pretreatment for removing the scale prior to the flaw detection. The surface of the member W becomes a glossy one (shot surface) after the shot blasting and reduces the emissivity $\epsilon$ so that the temperature difference $\Delta T$ detected by the radiation thermometer 9, i.e., the level of the flaw signal decreases. Furthermore, handling marks (for example, marks due to roller rubbing, bar applying or wire applying) are easily formed on the surface of the member, and these marks exhibit mirror-like appearance which is much more glossy than the shot surface so that the emissivity $\epsilon$ decreases significantly thereat. The part of lower emissivity $\epsilon$ is detected as a lower temperature part with the radiation thermometer 9. Therefore, it may be difficult to judge whether the low temperature part detected by the radiation thermometer 9 shows a real flaw or a handling mark. This leads to a false detection of regarding a handling mark as a real flaw and may lead to decrease in the detection accuracy.

The U.S. Pat. No. 3,020,745 discloses a technique wherein the surface of the member is uniformly covered with paint containing a black-body powder, such as carbon or graphite powder, for enhancing the emissivity $\epsilon$ of the member according to the heat radiation from the powder. This technique seems effective for achieving a high accuracy of flaw detection. Furthermore, the U.S. Pat. No. 3,504,524 teaches a non-destructive type of similar method wherein the painted layer is peeled off after flaw detection.

Although this is not a method for flaw-detection, the U.S. Pat. No. 4,408,903 discloses a method for measuring temperature of a member in hot-working process, such as hot-rolling or hot-forging, wherein carbon powder is electrodeposited on a surface of a long member in continuous transportation, whereby the heat radiation from the surface is homogenized, and high accuracy of temperature measurement is achieved. The member is generally heated by using an induction heating coil in such type of temperature measuring system. It is important to measure the member temperature just after heating in order to secure a precise temperature controlling condition in a hot-working process. For accomplishing such object, the U.S. Pat. No. 4,317,978 discloses an induction heating coil wherein the coil has a window for temperature measurement by a radiation thermometer.

Incidentally, when the flaw detection is performed on a member covered with scale, the handling marks by rolls, bars, wires, and so on, mentioned above may appear as parts of scale peeling off. The emissivity is smaller also for such parts than for the surroundings (scale), and the temperature measured with the radiation thermometer becomes lower thereat. This situation is fundamentally the same as that of the handling marks formed on the shot surface.

In this case, it appears that the thickness of the powder layer should be adjusted carefully for preventing such problem. In the prior arts, however, there is no disclosure or suggestion about the preferable powder layer thickness for preventing such false detection. A power layer on the member surface may prevent the heat from reflecting at the handling marks, which may lead to a false flaw detection. Too much thickness of coverage may, however, cause a decrease in heat radiation from the powder layer because a very thick powder layer is hardly heated to a sufficient temperature only by a heat conduction from the member. This may cause a decrease in the flaw-detection sensitivity due to a lower level of the flaw signal.

In this point of view, the powder layer seems to be preferably formed as thin as possible, as suggested in the U.S. Pat. No. 3,020,745. However, there is no disclosure on the preferable range of the thickness. For preventing the heat reflection at the handling mark, it seems to make a sense for a person having ordinary skill in the art that too thin powder coverage may increase exposing surface area without coverage on the member surface, whereby the effect in increasing the flaw signal due to the heat radiation from the powder layer cannot be expected sufficiently, and the probability of the false detection may increase because of a non-uniform powder coverage allowing partial exposure of handling marks. Therefore, the preferable configuration of the powder layer seems to be thin and uniform one, i.e., that without causing any surface exposure on the member, as suggested in the U.S. Pat. No. 3,020,745.

Furthermore, the important factor for achieving such uniform powder layer without causing exposure is not only the thickness thereof but also the particle diameter of the powder to be used. As shown in FIG. 35 (a), when the average thickness of the powder layer is fixed to t0, the layer consisting of particles with small diameter may hardly causes surface exposure since the particle layers may be multiply formed therein. On the other hand, as shown in FIG. 35 (b), the number of the particle layers decrease with increasing the diameter of the particle, and the member surface may expose at the interval between the particles. The U.S. Pat. No. 3,020,745, however, discloses no information about the preferable range of the powder layer thickness in relation to the powder diameter. Also in this case, it seems to make sense for a person having ordinary skill in the art that multilayered powder coverage as shown in FIG. 35 (a) is more preferable for preventing the exposure of the member surface.

The next problem is a configuration of the induction heating coil. Although the flaw detecting process has a technical similarity with the temperature measurement in the hot-working process in respect of measuring member temperature with a radiation thermometer, the technical purposes are completely different from each other. In the hot-working process, the member should be heated uniformly to high temperature so that the member is sufficiently softened for easy deformation. Therefore, a long coil is used for this purpose for securing a sufficient heating time as disclosed in the U.S. Pat. No. 4,317,978 wherein the coil length is almost ten times as long as the diameter of the coil cavity. In the case of flaw detection, however, such long coil causes an extreme decrease in flaw detection accuracy since the temperature difference between a flaw part and a sound part is completely vanished due to a long and uniform heating to high temperature.

The object of this invention is to enable a high accuracy of flaw detection even in the case that the surface emissivity of the member is not uniform because of the handling marks mentioned above, particularly by specifying the configuration or the morphology of the powder layer. Furthermore, it is also the object of this invention to make the flaw detection more easy and reliable by enhancing the total surface emissivity of the member and increasing the temperature difference $\Delta T$ (i.e., the flaw signal) on the surface.

SUMMARY OF THE INVENTION

For accomplishing the object mentioned above, the surface of the member to be inspected is covered with powder for making the surface emissivity uniform, the member is heated in this state, and then the flaws are detected by measuring the temperature distribution on the surface according to the energy emission therefrom.

That is to say, the flaw detection method of this invention comprises the following steps:

(1) forming a powder layer on the surface of the member by depositing dry powder thereon so that the surface is partly exposed by setting the average thickness of the powder layer is 0.1D–0.6D, where D is the average particle diameter of the powder, under an assumption that the powder particles in the powder layer are dispersed into a uniform thickness film;
(2) heating the surface region of the member according to a method of high frequency induction heating;
(3) measuring the temperature distribution on the surface of the heated member covered with the powder layer according to the energy emission from the surface of the member by using a radiation thermometer; and
(4) detecting the flaws on the member according to the temperature distribution on the surface of the member.

The most important point of the method is that the average thickness of the formed powder layer t0 is adjusted to be less than average diameter of the powder particle D, more specifically in a range of 0.1D–0.6D. The average thickness of the powder layer t0 is defined as a value in an assumption that the powder particles in the powder layer are dispersed into a uniform thickness film as shown in FIG. 35. By setting the thickness t0 to be in the range mentioned above, the member surface is partly exposed between the powder particles deposited on the member. The surface exposing ratio in the powder layer is to be determined by the average thickness t0 in relation to the powder diameter D.

As is described before, such exposure of the member surface seems to cause a decrease in flaw-detection accuracy for the person having ordinary skill in the art. The inventors discovered that partial surface exposure appears to be undesirable though, this partial exposure of the surface unexpectedly provides rather a good result. More specifically, the effect is not only that the flaw signal level is enhanced thereby increasing in the flaw-detection sensitivity, but also that false detection due to handling marks, and so on, is effectively suppressed, and the flaw-detection accuracy improves significantly. The mechanism thereof appears to be described as follows.

FIG. 8 (a) presents a schematic representation of the member surface with no powder coverage. Under an assumption that the member is an ideal black body, the value of energy emissivity $\epsilon$ is unity, and the energy emission Q is proportional to $T^4$ (Stefan-Boltzmann's law). The actual emissivity $\epsilon$ is, however, less than unity, and the energy emission becomes $\epsilon Q$ (<Q) since the member exhibits a certain level of energy reflection. In the area of a glossy surface, such as handling marks, the emissivity $\epsilon m$ becomes smaller than that $\epsilon n$ for the less glossy sound part, so that the energy emission $\epsilon mQ$ from the handling mark is to be smaller than that $\epsilon nQ$ from the sound part (i.e., $\epsilon mQ<\epsilon nQ$), whereby the handling mark may be misjudged as a flaw where the temperature level is lower than the surroundings.

On the other hand, as shown in FIG. 8 (b), when the member surface is covered with black body powder (such as carbons) so as to be partly exposed, and when the powder is heated to the same temperature as the member, the handling mark in the exposed area of the member surface reflects the energy Q radiated from the circumferential powders at a reflectance $\gamma m$, and this reflected energy $\gamma mQ$ is to be overlapped to the energy emission $\epsilon mQ$ therefrom. Therefore, the total energy from the handling mark area becomes to $\gamma mQ+\gamma mQ$. Similar phenomenon may occur also at the sound part, and the total energy from the sound part may be given as $\epsilon nQ+\gamma nQ$, where $\gamma n$ is the reflectance of the sound part surface.

The handling mark part is more glossy than the sound part, so that the reflectance $\gamma m$ of the handling part is smaller than that $\gamma n$ of the sound part. Therefore, the contribution of energy reflection is to be larger at the handling part $\gamma mQ$ that at the sound part $\gamma nQ$, i.e., $\gamma mQ>\gamma nQ$. Now, as is clear from the FIG. 8, the difference in the total energy between the handling mark part and sound part becomes smaller in comparison with that in the case of forming no powder coverage, and the apparent energy emission from the member surface is to be homogenized. Thus, the probability of false flaw detection decreases, and the flaw-detection accuracy improves significantly.

The energy from the powder is absorbed by the member W at an absorptance $\epsilon'$. For the member surface, the sum of the absorptance $\epsilon'$ and the reflectance $\gamma$ is unity, i.e., $$\epsilon'+\gamma=1 \tag{1}$$

On the other hand, the powder layer is formed on the member surface at a very small thickness, so that the particles deposited may be instantaneously heated by the member to the same temperature thereof as soon as deposited. Therefore, at the surface of the member, the absorptance $\epsilon'$ may be regarded to be almost the same as the emissivity $\epsilon$, i.e., $$\epsilon'=\epsilon \tag{2}$$

Therefore, from equations (1) and (2), $$\epsilon+\gamma=1 \tag{3}$$

The equation (3) means that at any exposed area on the member surface, the sum of its own energy emissivity $\epsilon$ and the reflectance $\gamma$ for the external energy (i.e., from the particles deposited) is maintained to be nearly equal to unity regardless of the existence of a glossy portion such as an handling mark. That is to say, at the part of handling mark, $$\epsilon mQ+\gamma mQ=(\epsilon m+\gamma m)Q=Q \quad (4),$$

and at the sound part, $$\epsilon nQ+\gamma nQ=(\epsilon m+\gamma m)Q=Q \quad (5).$$

Therefore, when the surface exposing ratio at the powder layer is adjusted to be a proper value, the apparent energy emission from these two parts are almost the same each other, so that the probability of false flaw detection due to the handling marks becomes very small.

When the average thickness of the powder layer t0 is less than 0.1D, the surface exposing ratio becomes too large, and very large exposing area may be formed too much. In such large exposing area, the energy from the surrounding particles hardly reaches to the central part thereof since the distance to the nearest particle becomes too large, so that the effect of aforementioned energy reflection cannot be expected. This leads to a decrease in the flaw-detection accuracy. On the other hand, average thickness t0 exceeding 0.6D leads to a decrease in the flaw signal level, i.e., flaw-detecting sensitivity, since the powder layer becomes too thick to be heated to a sufficient temperature only by a heat conduction from the member. The thickness t0 is preferably adjusted in a range of 0.25D–0.5D.

The inventors also discovered that it is preferable to form a powder layer on the surface of the member by depositing dry powder thereon so that the surface is partly exposed with a surface exposing ratio of 2–70%. When the surface exposing ratio exceeds 70%, the surface exposing ratio becomes too large, and the effect of aforementioned energy reflection cannot be expected. This leads to a decrease in the flaw-detection accuracy. On the other hand, the surface exposing ratio less than 5% leads to a decrease in the flaw signal level, i.e., flaw-detecting sensitivity. The surface exposing ratio is preferably adjusted in a range of 5–40%.

One example of the members to be inspected are those having surfaces treated by shot blasting (shot surface), but the members are not limited to such ones, and those covered with scale are also adopted for the flaw detection.

In the step of covering the member with powder mentioned above, the powder can be deposited on the surface of the member by using an attractive force of static electricity, and so on. This powder coverage can be formed by using a technique of electrodeposition wherein the powder and the member are charged negative and positive respectively. After the powder coating, the high frequency induction heating and the subsequent temperature measurement with a radiation thermometer are performed, and then flaws are detected according to the temperature distribution on the surface. The temperature at the flaw to be detected becomes higher or lower than at the sound part depending upon whether the depth of the permeation of the induction current for heating is larger or smaller than the depth of the flaw to be detected, or depending upon the morphology of the flaw.

It is preferable to remove the powder deposited on the surface of the member after finishing the measurement of the temperature distribution on the surface. In this powder removing step, the powder deposited on the member is sucked by a vacuum cleaner or blown away by using high pressure air from a nozzle or from a blower.

When the member consists of a non-magnetic material (a non-magnetic stainless steel, and so on), the penetration depth of the high frequency induction heating is set to be larger than that of the flaw to be detected in the method of this invention. The flaw is detected according to that the temperature is lower on the parts where flaws exist than on the parts where no flaw exists.

As shown in FIG. 37, an induction current (eddy current) is generated in the surface region of the member W by the induction heating coil 8. When the penetration depth of the induction current ($\delta$) is set to be larger than that of the flaw to be detected (d), the temperature at the flaw, in most of the cases, becomes lower than that of the surroundings since the induction current passes around the flaw thereby causing a reduction of current density thereat, as shown in FIG. 31 (the temperature is conceptually expressed by a length of an upward arrow in FIG. 31). The flaw can be detected by measuring the temperature difference $\Delta T$ with the radiation thermometer 9. On the other hand, there may be the case that the temperature at the flaw is higher than the sound part (the part with no flaw) depending upon the morphology of the flaw, for example, in the case of a spot-like flaw or a flaw consisting of spots formed in a row. Particularly, the flaws on the edge portion of a square bar is detected as a high temperature part in most of the cases.

For a magnetic material, the depth of the electric current permeation of high frequency induction heating, $\delta_0$, is usually smaller than that of the flaw to be detected, d, as shown in FIG. 33. Since the electric current density is larger for the flaw part than for the sound part, the heat generated by the induction heating is larger for the flaw part, and the temperature measured by the radiation thermometer 9 becomes higher thereat. In this case, the part where the temperature is higher than its surroundings is to be judged as a flaw. The flaw part should be measured as a high temperature part with the radiation thermometer 9 if the flaw detection principle presented in FIG. 33 is adopted, but when the flaw part exists, for example, within a handling mark S1 as shown in FIG. 34, the apparent temperature at the flaw part becomes low because of the small emissivity due to the handling mark. In this case, the flaw detection may result in fail. Such problem, however, can be prevented in this invention since the powder coverage provides a uniform emissivity.

The apparatus of this invention for detecting flaws comprises;

(1) a transportation line for transporting a member to be inspected;
(2) a powder deposition device mounted on said transportation line for covering the surface of the member with powder at the condition of the method of this invention mentioned above;
(3) a high frequency induction heating device mounted on the transportation line for heating the surface region of the member;
(4) a radiation thermometer for measuring the temperature distribution on the surface of the heated member covered with the powder; and
(5) a detecting device for detecting flaws on the member according to the temperature distribution.

On the transportation line of the apparatus of this invention, a powder removing device can be mounted for removing the powder deposited on the surface of the member. For enhancing the reliability of flaw data, it is important that the radiation thermometer measures the temperature distribution on the surface of the member heated by the high frequency induction heating device while the temperature drop is as small as possible. Therefore, the radiation thermometer is preferable to measure the temperature just after heating or during heating. The high frequency induction heating device is usually equipped with a heating coil into which the member to be inspected is inserted. The temperature measuring point can be arranged, for example, just next to the heating coil on the transporting line or can be located in the heating coil.

The high frequency induction heating device is preferably constituted as to comprise a heating coil having a cavity into which the member is inserted, and wherein the Lc/Dcmax is less than ½, where Lc is the coil length and Dcmax is the maximum cross sectional dimension of the cavity. Lc/Dcmax exceeding ½ may make the member heating time too long thereby causing the decrease in the flaw-detection accuracy due to the degeneration of the temperature difference between the flaw part and the sound part. Dcmax is preferably set to be less than ¼.

For example, the apparatus can be constituted so that the induction heating device comprises a heating coil wherein an aperture (slit, notch, hole, and so on) formed therethrough from the inside to the outside thereof, and the radiation thermometer receives the energy emitted through the aperture. The apparatus can also be constructed so that the radiation thermometer located on the direction inclined to the heating coil which receives the energy emitted through the gap between the heating coil and the member inserted thereinto. Particularly for non-magnetic steels, the absorption of electric power is smaller than for magnetic steels so that the flaw detection is needed to be performed at a low transportation speed. In this case, the temperature measurement is performed preferably in the heating coil for avoiding the temperature drop due to heat conduction, which causes the degeneration of the temperature difference between the flaw part and the sound part, as small as possible.

Following subjective matters can be added to the apparatus of this invention.

(1) said radiation thermometer which detects the temperature distribution on the surface of the member in transportation along a predetermined detecting line set in a direction crossing with the transportation direction of the member;
(2) a temperature distribution data generating means which performs the sampling of the output from the radiation thermometer at a designated sampling timing, thereby generating temperature distribution profile data along the detecting line at the position determined on the surface of the member corresponding to the sampling timing;
(3) a sampling commander which commands the temperature distribution data generating means to perform the sampling at a designated time interval corresponding to the transportation speed of the member so that the temperature distribution data generating means generates plural sets of the temperature profile data which correspond to different positions on the surface of the member in the transportation direction;
(4) a flaw data generating means which generates flaw data at least for specifying the flaw position on the surface of the member according to the sets of temperature profile data.

According to this configuration, a set of flaw data may be obtained very efficiently.

Furthermore, following subjective matters can be added;

(5) a flaw removing device which is movable along the surface of the member and removes a flaw existing on the surface;
(6) a moving mechanism which moves the flaw removing device independently in two or more directions crossing each other so as to be able to position the flaw removing device at an arbitrary site on the surface of the member;
(7) a moving commander which commands the moving mechanism to move the flaw removing device to the flaw site determined according to the flaw data.

According to this configuration, subsequent flaw removing process can be performed automatically referring to the flaw data obtained. The flaw removing process can be performed after the transportation of the member has been stopped. More specifically, a member supporting means for supporting the member so as to be fixedly positioned in a designated site can be added. The flaw removing device removes the flaw on the member supported by the member supporting means.

A bar-like member with a square-like axial cross section can be used as the member to be inspected. In this case, the bar-like member can be transported in the longitudinal direction thereof so that one diagonal line of the square-like axial cross section is almost vertically directed. Corresponding to this transportation configuration, the transportation line can comprise a pair of member transportation rollers which pinches the member from above and below, respectively, and whose roller surface has a V-shaped cross section corresponding to the corner shape of the square-like axial cross section of the member. According to this constitution, the member can be transported stably, and the accuracy of the flaw-detection may improves.

BRIEF DESCRIPTION OF THE DRAWINGS

In the accompanying drawings:

FIG. 9 is a cross-sectional view showing the flaw detection process for the member;

FIG. 16 is a schematic illustration of the main part of the flaw detecting apparatus in FIG. 1;

FIG. 35 is a figure presenting the concept of the average thickness of the powder layer;

DETAILED DESCRIPTION OF THE PREFERABLE EMBODIMENTS

Several embodiments of this invention will now be described with reference to accompanied drawings.

Figure 1:
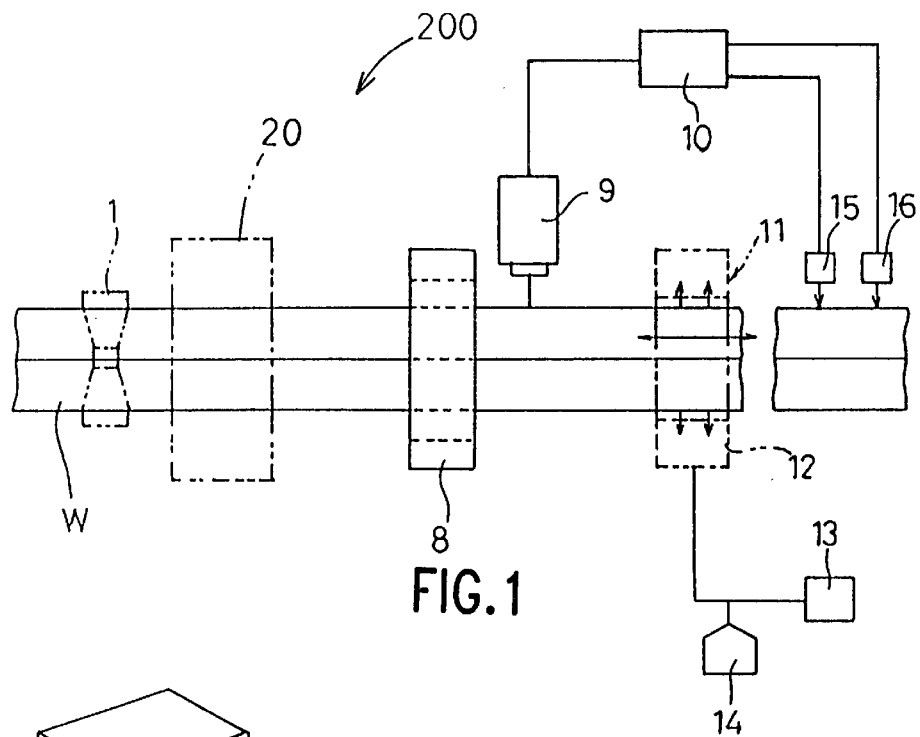
FIG. 1 is a figure conceptually presenting the flaw detection method and the apparatus of one embodiment of this invention.

In FIG. 1, the member to be inspected (simply as 'the member', hereinafter) W consists of a non-magnetic material formed in a longitudinal shape having a square cross-section, and its outer surface presents, for example, a shot one as a result of removing the scale through shot blasting, and so on. This member W is transported by the transportation line comprising pairs of bobbin-shaped member transportation rollers 1, and so on.

Figure 5:
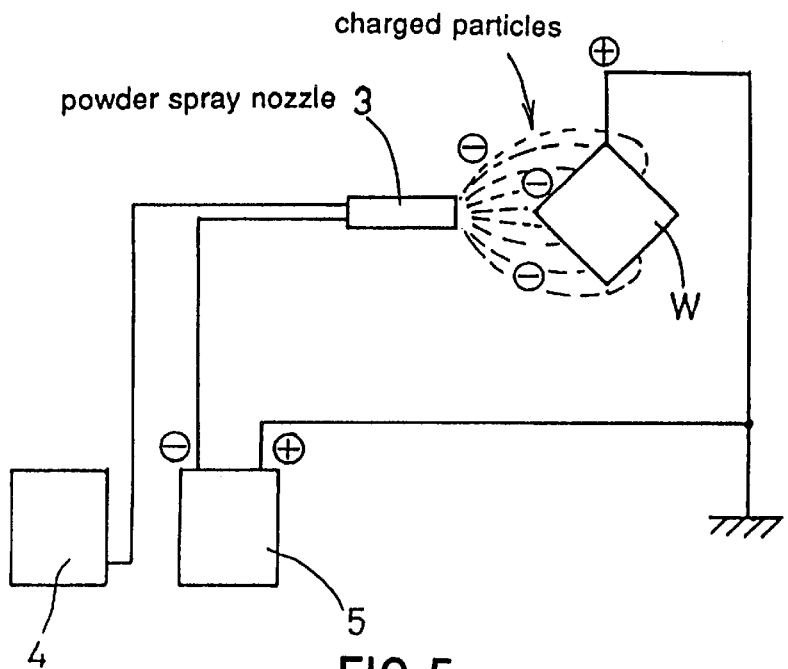
FIG. 5 is a figure presenting the principle of electrostatic powder coating.
Figure 6:
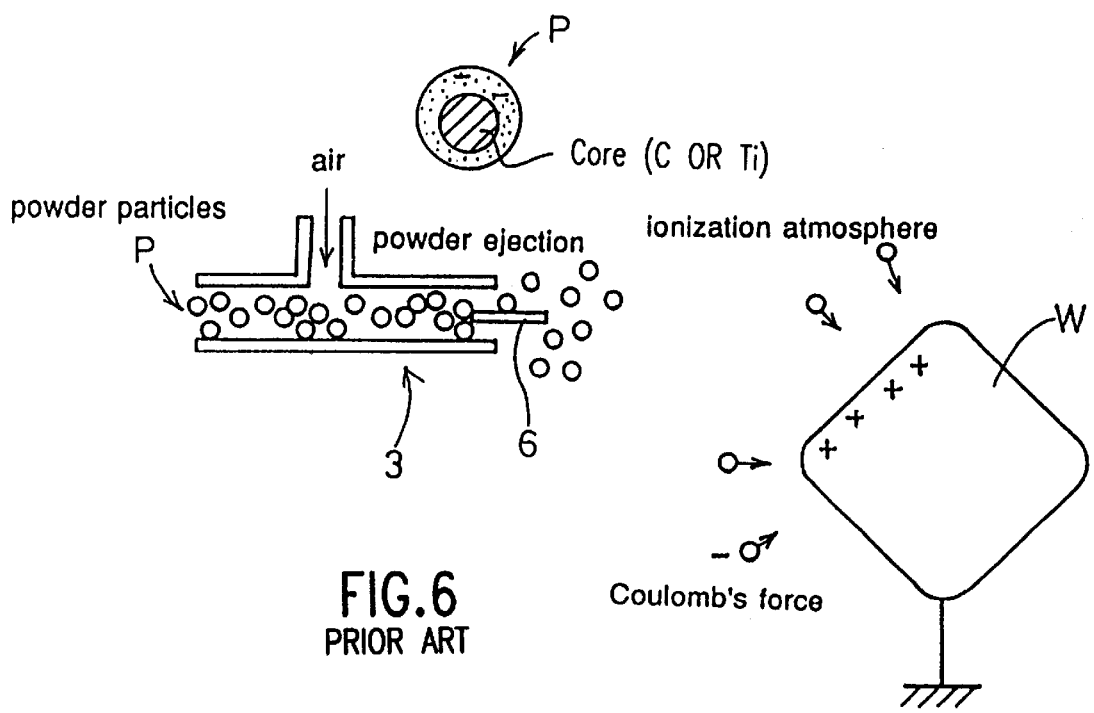
FIG. 6 is a figure showing the detail of FIG. 5.

A powder deposition device 20 is mounted on the transportation line. This device deposits designated powder on the surface of the member W by using static electricity, and the principle of the deposition is the same as that of a conventional electrostatic powder coating. FIG. 5 and FIG. 6 conceptually show the principle of the powder coating. The designated powder is fed to the a powder spray nozzle 3 from a powder tank 4. A high voltage power generator 5 applies an voltage between the powder spray nozzle 3 and the member W at negative polarity for the spray nozzle 3 and at positive polarity for the member W. The member W is grounded.

As shown in FIG. 6, each powder particle P, for example, has a core consisting of C (carbon) or Ti (titanium) and a shell consisting of resin (for example, acrylic resin, and so on). The average particle diameter is, for example, approximately in the range of 10–100 $\mu$m. The average diameter of particles is preferably 20–50 $\mu$m and more preferably 40 $\mu$m because of an economical reason. The resin shell of the particles P are negatively charged under an ionization atmosphere formed by the voltage mentioned before (for example, 100 kV with up to 50 $\mu$A of current), attracted to the member W in the anode side by the Coulomb's force and cover its surface depositing thereto. The average thickness t0 of the powder layer is adjusted to be in a range of 0.1D–0.6D, and preferably in a range of 0.25D–0.5D. The average thickness of the powder layer t0 is defined as a value in an assumption that the powder particles in the powder layer are dispersed into a uniform thickness film as shown in FIG. 35. Furthermore, the surface exposing ratio is adjusted in a range of 2–70%, and preferably in a range of 5–40%.

Figure 7:
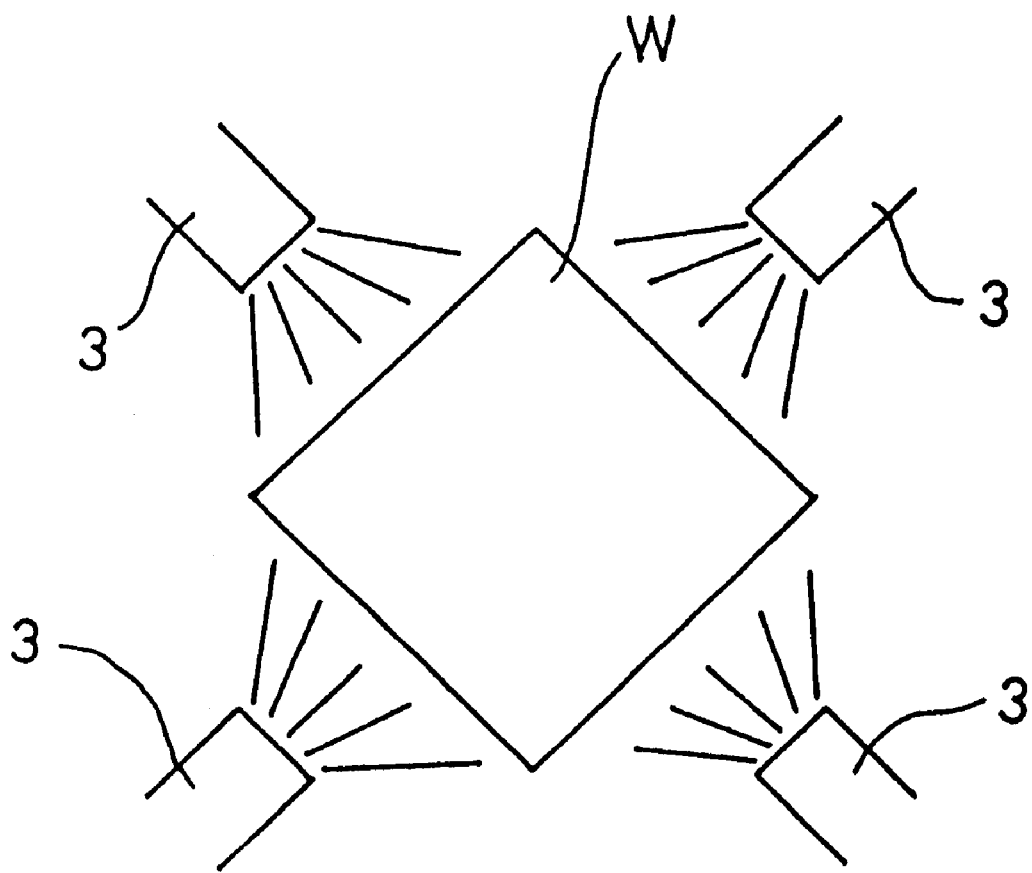
FIG. 7 is a figure explaining an example of powder coating.
Figure 8A:
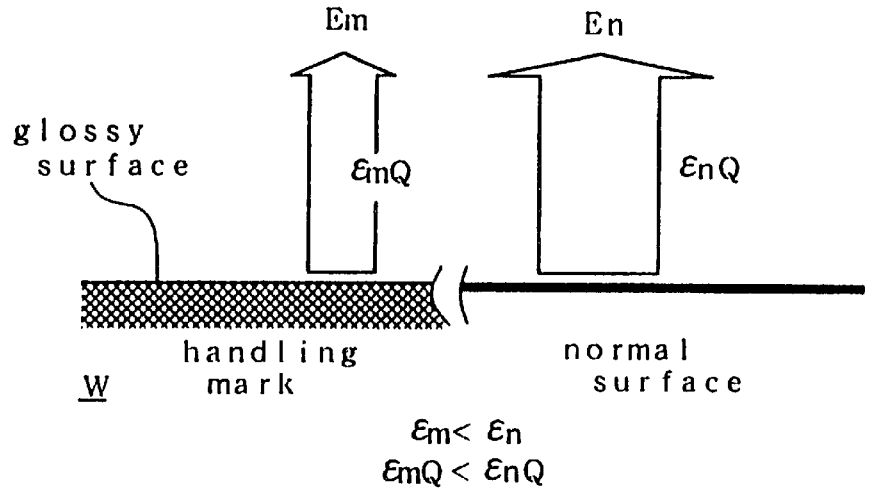
FIG. 8 is a figure explaining the effect when the powder is deposited at a very small thickness so that the surface of the member is partly exposed.
Figure 8B:
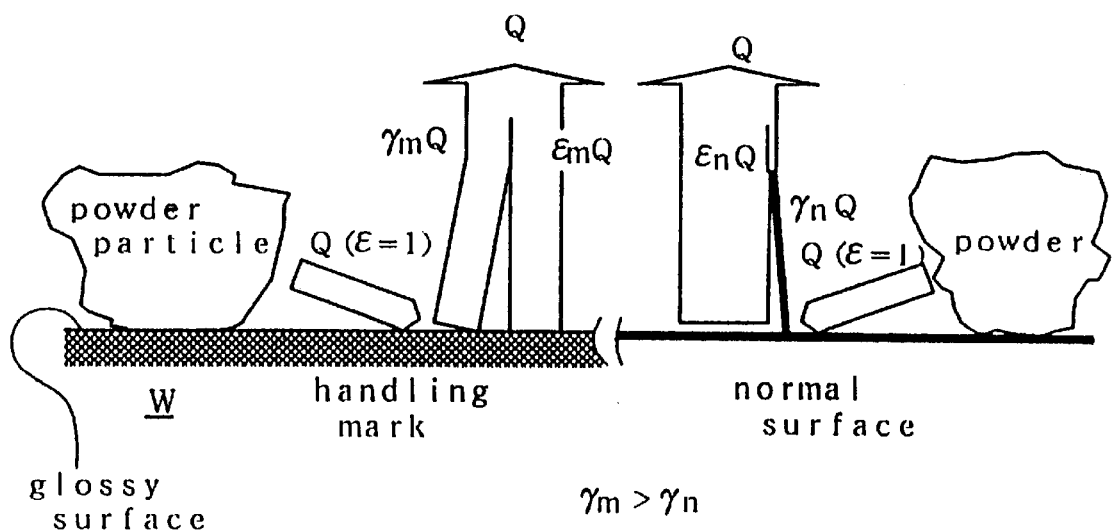

As shown in FIG. 7, for example, the powder spray nozzle 3 can be constituted to be able to cover each surface of the member W with the powder individually along the direction of the transportation. In this case, all surfaces of the member W can be coated simultaneously with the powder also by using four such powder spraying nozzles 3 arranged around the member W. The member W can be coated with the powder by using only one spray nozzle 3 in such way that one half side of the member W is coated by the spray nozzle 3, then the member W is turned and taken back to the upper stream in a reciprocal motion, and finally the other half side is coated by the same nozzle 3.

As shown in FIG. 9 (a), for example, if handling marks S1 are existing on the surface S of the member W, the surface emissivity of the member W becomes almost uniform since the surface S of the member W, having the handling marks S1 thereon, is coated with the powder particles P (FIG. 9 (b)). There is no limitation upon the color of the powder particles. The powder particles P deposited on the surface S of the member W are bad conductors and maintain negative charge so that the particles never drop from the surface S within a certain period even if the member W is cut from the ground.

When the member W is treated by shot blasting, the surface S becomes a shot surface, and the handling marks S1 formed by rolls, bars, wires, and so on, have mirror-like appearances which are more glossy than the shot surface. On the other hand, when the member W is the one covered with scale before shot blasting, the surface S and the handling marks S1 correspond to the scale and the parts of scale peeling off, respectively. The surface S is, however, a shot one in many cases.

Figure 3:
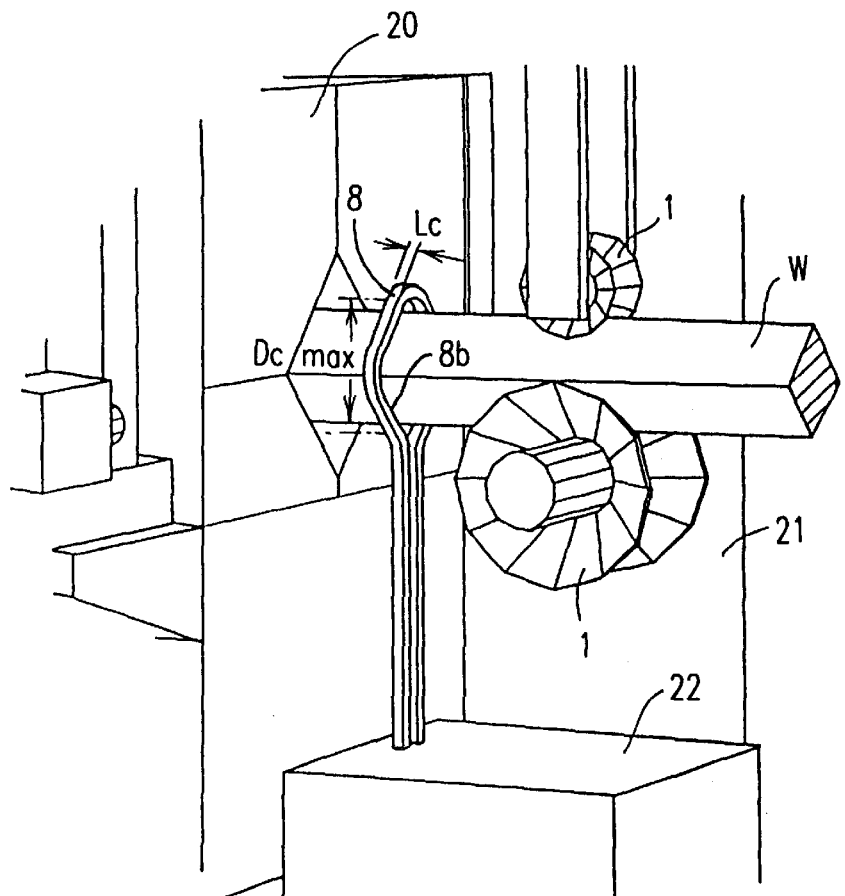
FIG. 3 is a partial enlarged view of FIG. 2.
Figure 31:
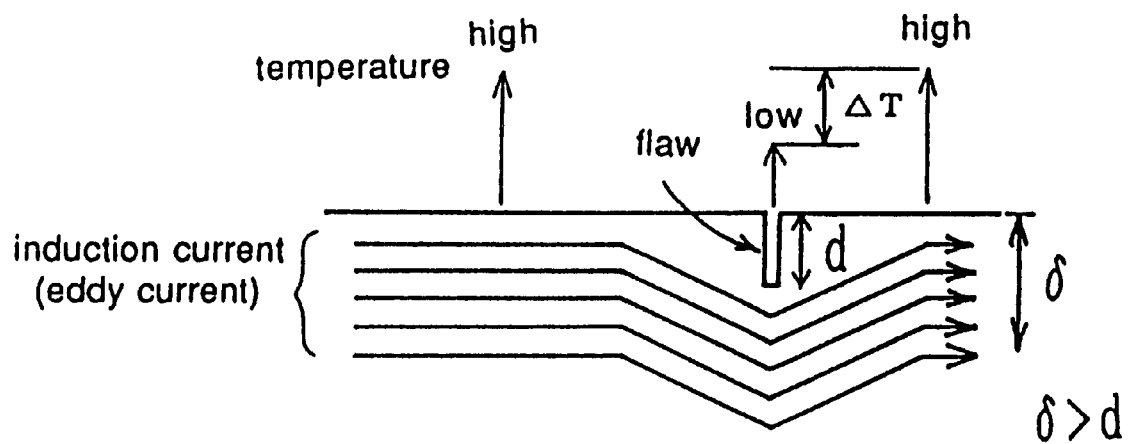
FIG. 31 is a figure explaining the relationship between the position of the flaw and the path of the induction current.
Figure 32:
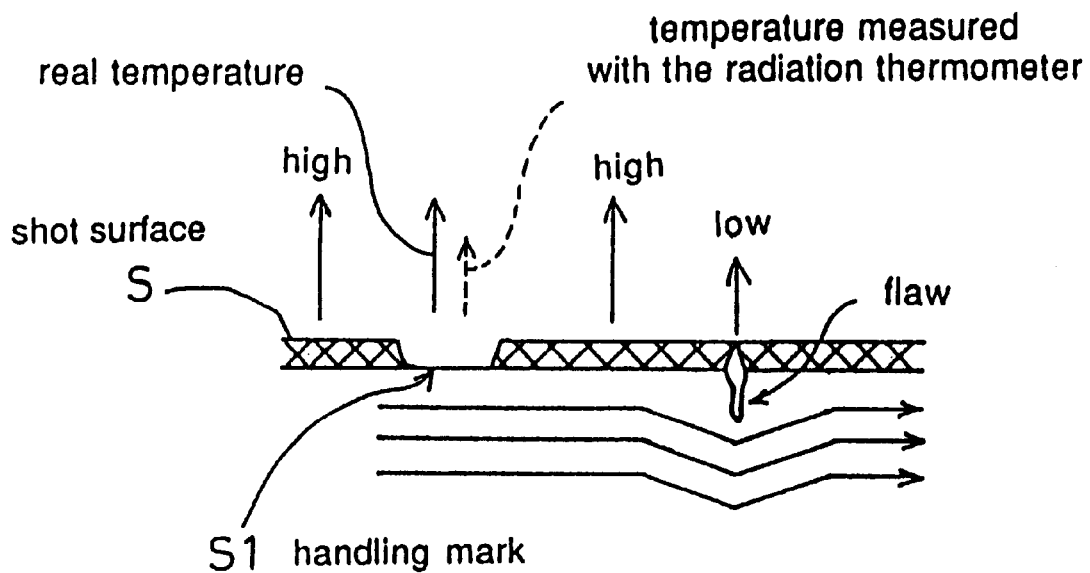
FIG. 32 is a figure explaining the energy emission in the case that a handling mark exists on the member.
Figure 33:
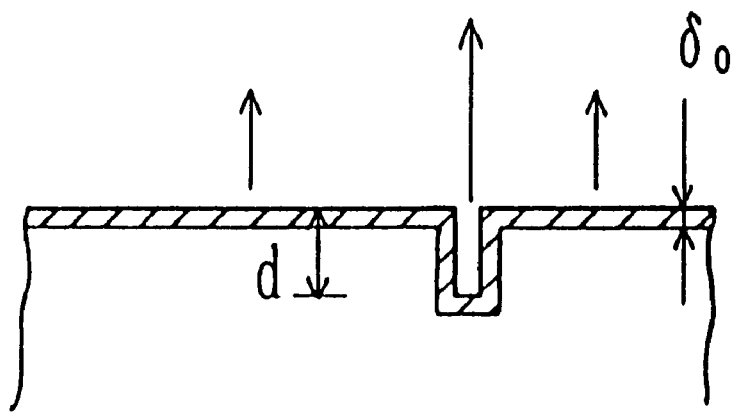
FIG. 33 is a figure explaining the case that the depth of the electric current permeation in the surface region of the member is smaller than the depth of the flaw.
Figure 34:
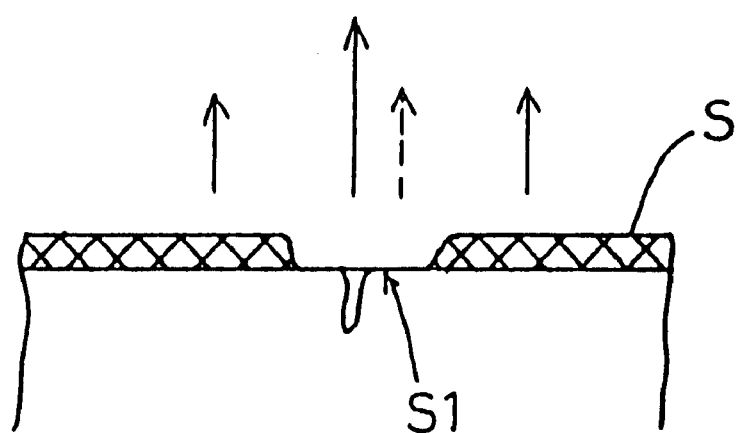
FIG. 34 is a figure showing the case that a flaw exists within a handling mark.
Figure 36:
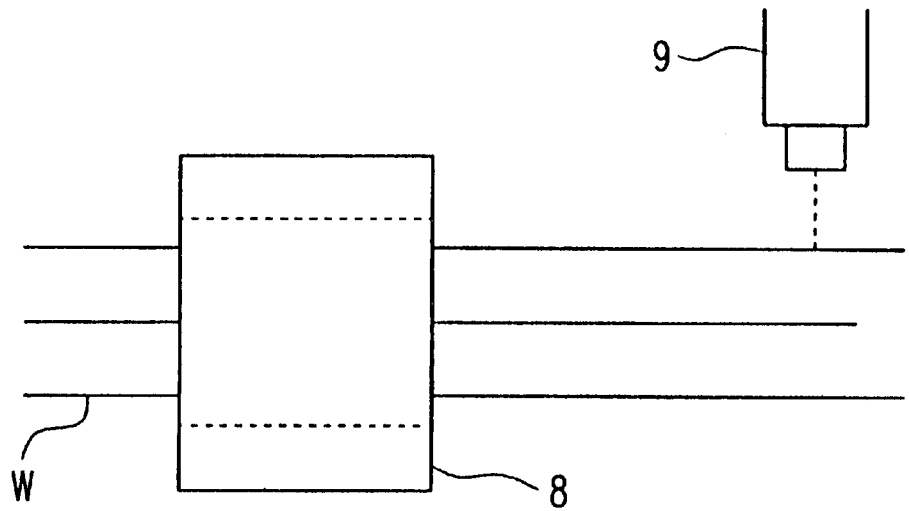
FIG. 36 is a perspective view presenting an example of a conventional flaw detection method.
Figure 37:
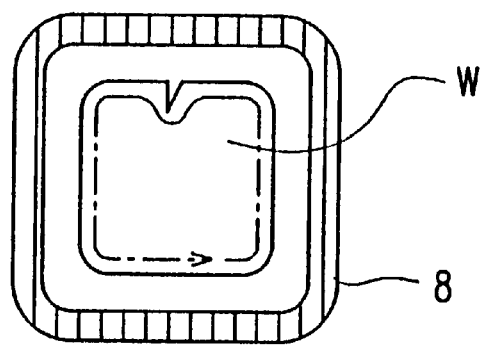
FIG. 37 is a cross-sectional view of the coil for high frequency induction heating in FIG. 36.

As shown in FIG. 1, a high frequency induction coil ("coil", hereinafter) 8 as a heating device is mounted on the lower stream of the transportation line. This coil 8 is a one for generating an induction current (eddy current) in the surface region of the member W, and formed in an annular shape surrounding the member W as shown in FIG. 3. The coil 8 has a cavity into which the member W is inserted, and wherein the Lc/Dcmax is less than ½, where Lc is the coil length and Dcmax is the maximum cross sectional dimension of the cavity 8b. For the member W consisting of a non-magnetic material, the induction frequency is set so that the depth of current permeation, $\delta$ (FIG. 31), is larger than the depth of the flaw to be detected, d.

As shown in FIG. 9 (c), the surface region of the member W is heated by the induction current (eddy current) generated therein. Except for the cases of flaws or cracks on the edge portion of a square bar, and so on, which exhibit higher temperature than in the sound part, the induction current passes around the flaw so that the temperature becomes lower at a flaw than at a sound part in most of the cases. The temperature of the member W increases 20–30° C. from ambient temperature by heating as mentioned above, i.e., the member W is heated to 40–50° C. when the ambient temperature is 20° C.

In FIG. 1, a radiation thermometer 9 is arranged just next to the induction heating device 8 and measures the surface temperature of the member W whose surface region is heated. The radiation thermometer 9 is a conventional one which transforms the energy emission from the surface of the member W into an electric output by using sensors and displays this output. A plurality of such radiation thermometers 9 are arranged in the apparatus of FIG. 1, and each thermometer 9 corresponds to one face or one edge of the member W.

Figure 11:
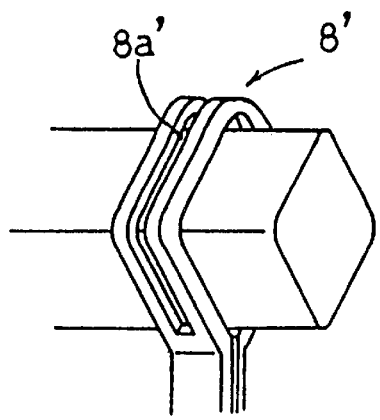
FIG. 11 is a figure showing the case of using a coil wherein a slit is formed in the center portion.
Figure 12:
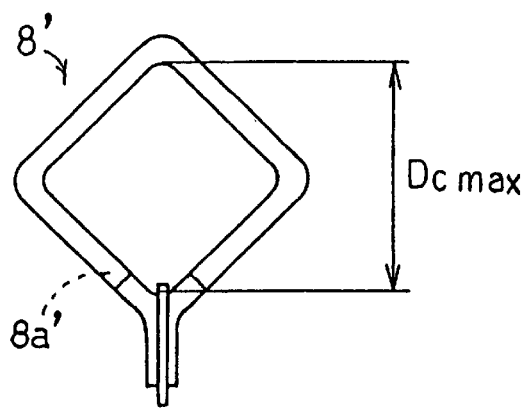
FIG. 12 is a front view of FIG. 11.
Figure 13:
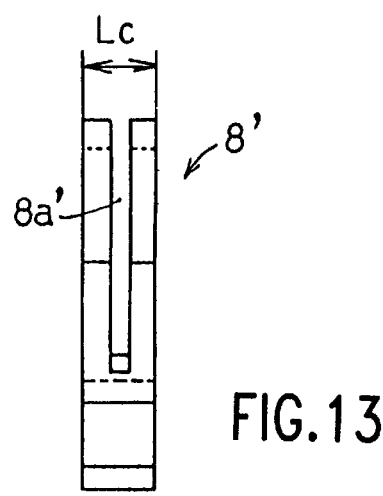
FIG. 13 is a side view of FIG. 11.
Figure 14:
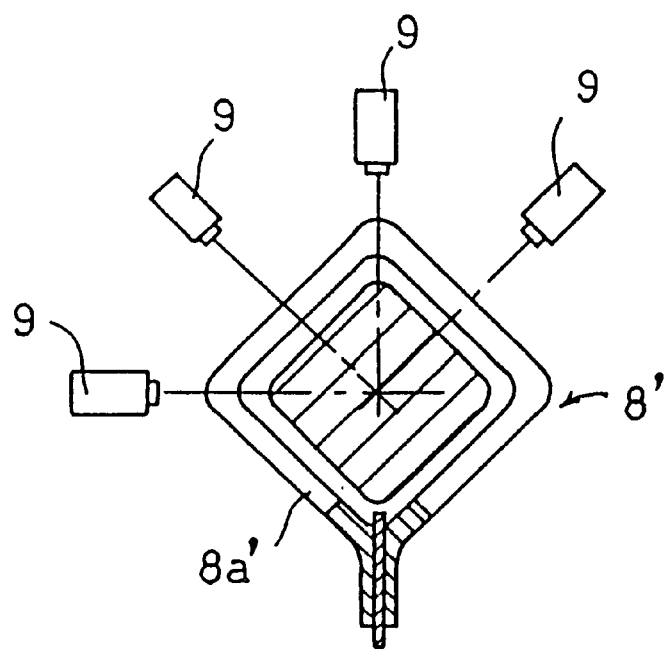
FIG. 14 is a figure explaining the first example of the case that the temperature measurement for the member is performed in the heating coil.

As shown in FIGS. 11–13, a fork type of heating coil 8', in other words, a coil 8' having a cavity (such as slit 8a) formed therethrough from the inside to the outside thereof can be used. The member W is inserted into the coil 8' and heated therein. The surface temperature of the part heated is measured in the coil 8' by using appropriate number of radiation thermometers 9' through the slit 8a' as shown in FIG. 14. Such temperature measurement in the heating coil 8' provides a high accuracy of measurement since almost no temperature drop occurs.

Figure 15:
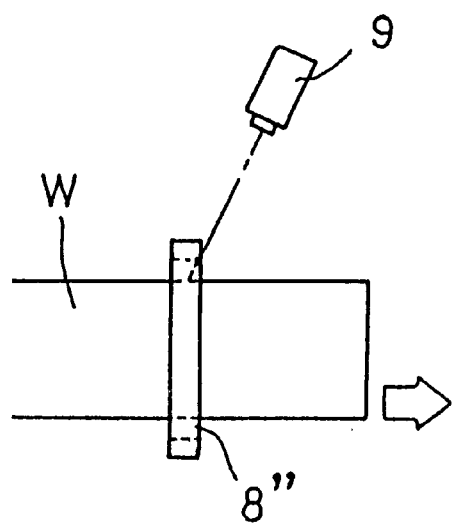
FIG. 15 is a figure explaining the second example of the same case.

The same effect can be obtained also by using the device presented in FIG. 15. In this case, the radiation thermometer 9 is arranged in the position and direction so that it is directed to the member W in the heating coil 8" through the gap between the heating coil 8 and the member W inserted therein.

Figure 27:
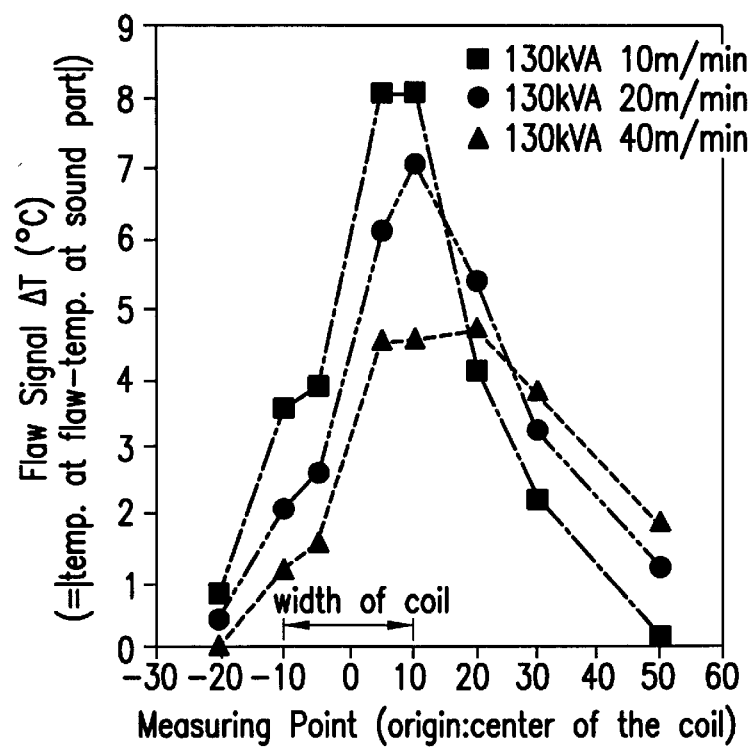
FIG. 27 is a figure explaining the first graph of the case that the temperature measurement is performed for the member in the heating coil.
Figure 28:
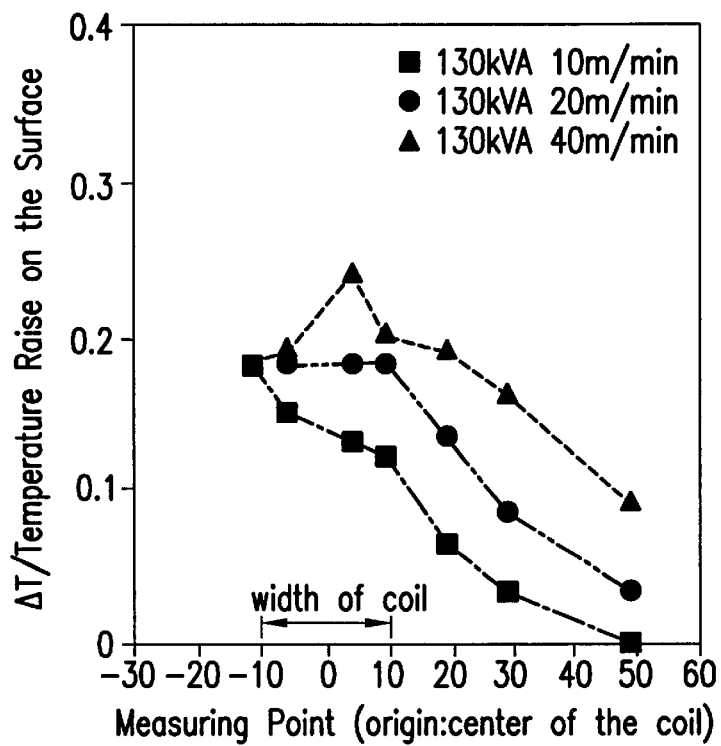
FIG. 28 is a figure explaining the second graph of the same case.

FIG. 27 is a graph presenting the sensitivity (intensity) of the flaw signal ΔT measured along the direction parallel to the center axis of the heating coil 8 which is defined as the origin. The electric power supplied to the heating coil 8 was fixed to 130 kVA, and three transportation speeds of the member W (relative to the coil 8) were used, i.e., 10 m/min, 20 m/min and 40 m/min. According to this result, regardless of the transportation speed, it is preferable to measure the temperature at around the region from the center to the exit of the heating coil 8 for enhancing the level of the flaw signal ΔT. FIG. 28 shows the ratio of the flaw signal ΔT to the temperature raise at the surface of the member W (i.e., the degree of how strong a flaw signal is obtained against the temperature raise). Good results are obtained within the width of the heating coil 8.

Figure 10A:
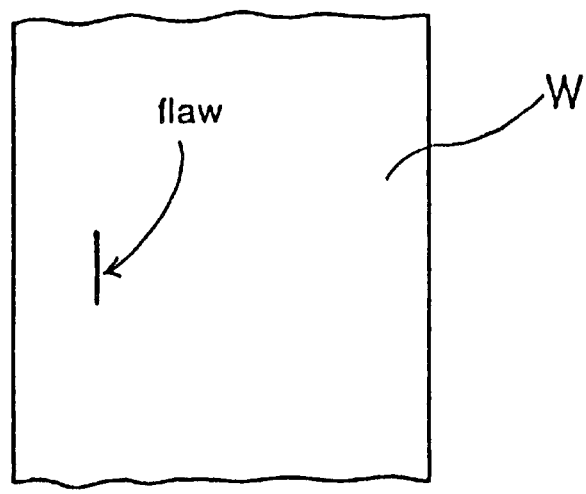
FIG. 10 is a figure showing the relationship between the flaw existing on the member and the temperature measured by the radiation thermometer.
Figure 10B:
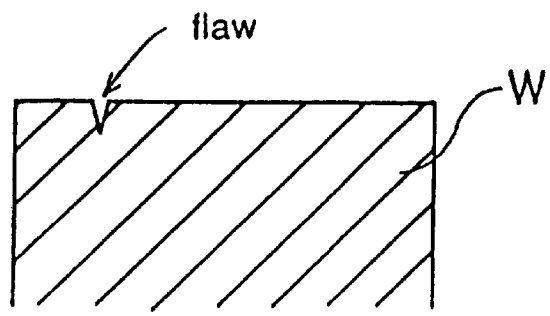
Figure 10C:
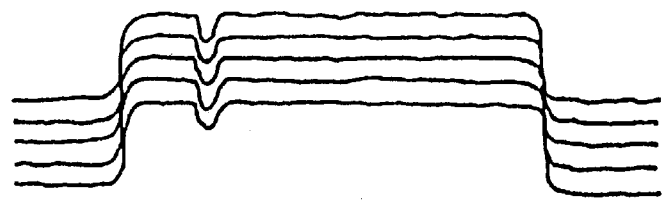

If a flaw exists on the surface of the member W as shown in FIG. 10 (a) and (b), for example, the temperature distribution measured by the radiation thermometer 9 becomes as shown in FIG. 10 (c). Even if a handling mark S1 exists as shown in FIG. 10 (a), the mark S1 is covered with the powder P so that the surface emissivity of the member W becomes almost uniform, and the temperature measured by the radiation thermometer 9 does not exhibit a lower value at the handling mark S1. Therefore, the handling mark S1 is never detected falsely as a flaw.

As shown in FIG. 1, on the lower stream side of the radiation thermometer 9, there are a powder removing device 11 equipped with a suction portion 12 mounted as surrounding the member W, a suction pump 13 connected with the suction portion 12 and a powder collection portion 14. This device removes the powder deposited on the member W by sucking and collects the powder after the temperature measurement with the radiation thermometer 9. The suction portion 12 of the powder removing device 11 can be mounted movably along the longitudinal direction of the member W.

Figure 2:
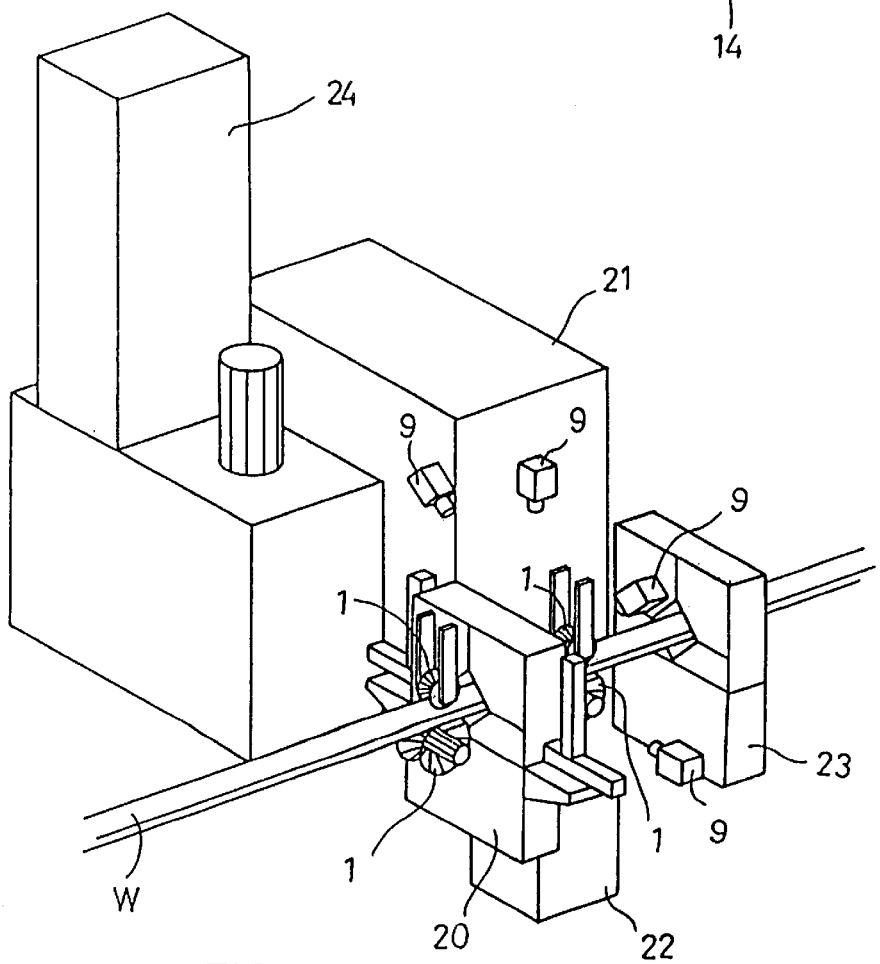
FIG. 2 is a perspective view specifying the concept of the apparatus presented in FIG. 1.
Figure 4:
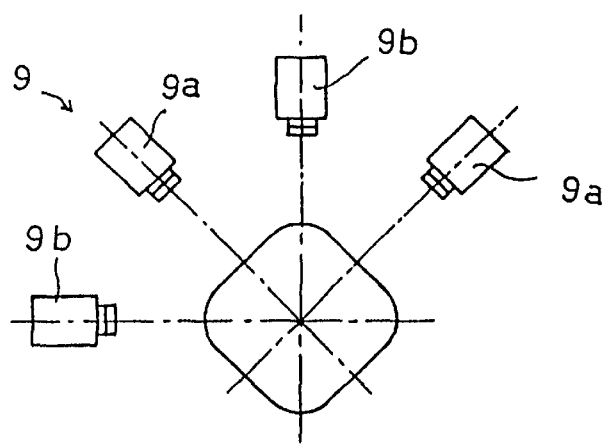
FIG. 4 is a figure showing the arrangement of the radiation thermometer in FIG. 2.

FIG. 2–FIG. 4 shows an apparatus which specifies the conceptual image of the apparatus presented in FIG. 1. In FIG. 2, a steel member W is transported by plural pairs of member transportation rollers 1 in its own longitudinal direction. When the steel member W passes through the powder deposition device 20, the powder is electrostatically deposited on the surface of the member W. In the powder deposition device 20, there are, for example, two powder spraying guns (not drawn in the figures) each of which corresponds to one face or one edge of the steel member W. On the lower stream side of the powder deposition device 20, a heating coil 8 as shown in FIG. 3 is mounted, and a high frequency current is supplied thereto from a power source 21 via a coil transformer 22.

During the step of passing through the heating coil 8, the steel member W is heated, and the powder deposited thereon is heated by the heat transfer from the member W. On the lower stream side thereof, a plurality of radiation thermometer 9 are mounted as shown in FIG. 2. These radiation thermometer 9 are arranged, for example, with two for the faces 9a and two for the edges 9b (i.e, four in total), and measure the temperatures on a half side of the member in one measurement. On the further lower stream, there is a powder collecting box 23 as shown in FIG. 2, which collects the powder from the surface of the steel member W. The flaw detection is performed to one side of the steel member W in one cycle of measurement, and then performed for the other half side in the next cycle after returning the member W to the upper stream or transporting the member W to the further lower stream.

Although the flaw existence can be judged through a visual observation of the temperature distribution according to the values measured by the radiation thermometer 9, the apparatus can be constituted so that the radiation thermometer 9 is connected with a judging means 10 comprising a computer, and so on, and the apparatus makes a warning signal when the judging means 10 detects a temperature abnormality, with showing the data of the flaw detected such as the location, depth, and so on, on a displaying means as conceptually shown in FIG. 1. The apparatus can comprise a marking device 15 which makes a mark indicating the location of the flaw when receiving a signal from the judging means 10. Furthermore, the apparatus can comprise a grinder 16 which removes detected flaws automatically receiving a signal of flaw location from the judging means 10.

FIG. 16 is a schematic illustration of the main part of the flaw detecting apparatus 200 in FIG. 1. The member W has a square-like axial cross section and is transported in its longitudinal direction so that one diagonal line of the cross section is vertically directed by the pair of bobbin-shaped member transportation rollers 1,1. The member transportation rollers 1,1 pinches the member W from above and below, respectively, and are driven by a servo motor 120 so as to rotate oppositely each other for transporting the member W. The roller surface of each roller 1 has a V-shaped cross section corresponding to the corner shape of the axial cross section of the member W.

The rotation speed of one of rollers 1,1 is detected by a pulse generator ("PG", hereinafter) 105 for detecting the member transportation speed. Furthermore, on the upstream of the heating coil 8, a member detecting sensor 112, such as a photo electric sensor, is arranged for detecting the arrival of the front end of the member W. In this embodiment, the radiation thermometers 9 (only one is presented in FIG. 16) detects a line-profile of temperature distribution and are arranged along the upper sides of the slit 8a of the coil 8 for detecting the temperature distributions along the widths of corresponding upper side surfaces of the member W, respectively.

Figure 17:
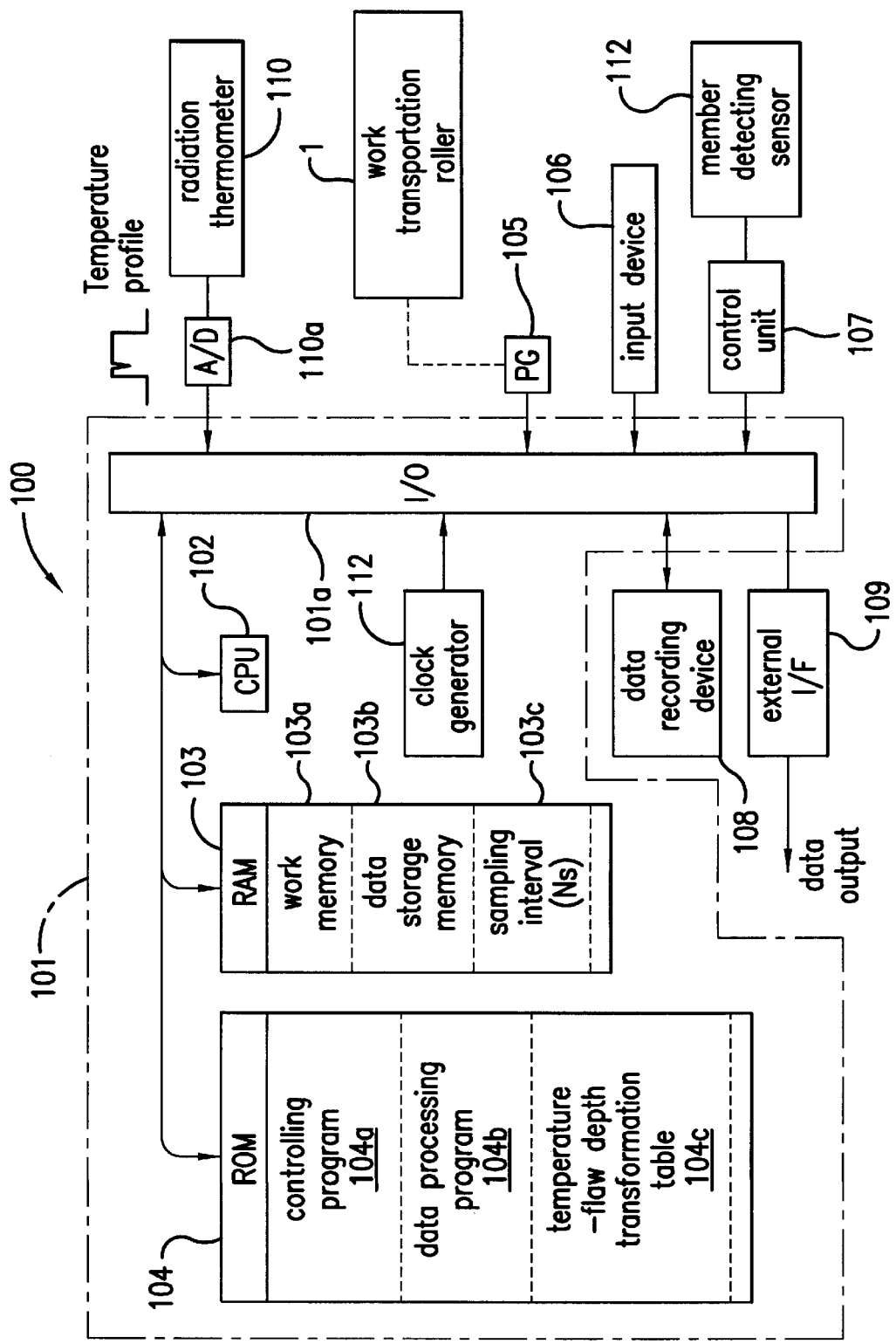
FIG. 17 shows an block diagram of a controlling unit of the flaw detecting apparatus.

FIG. 17 shows a block diagram of a controlling unit of the flaw detecting apparatus 200. The controlling unit 100 comprises a micro processor 101 having an I/O port 101a, and CPU 102, RAM 103 and ROM 104 connected thereto. To the I/O port 101a, A/D converter 110a, PG 105, input device 106 such as a key board, sensor control unit 107, external interface 109, data recording device 108 such as an hard disk drive, and clock generator 111 are connected, respectively. The radiation thermometer 110 and the member detector 112 are connected to the A/D converter 110a and the sensor controlling unit 107, respectively. The CPU 102 functions as a temperature distribution data generating means and a sampling commander.

In the RAM 103, a work memory 103a for the CPU 102, a data storage memory 103b, and a memory 103c for storing a value of sampling interval Ns (input from input device 106, for example) are formed. On the other hand, the following programs and data are stored in the ROM 104: a controlling program 104a, a data processing program 104b, and a temperature-flaw depth transformation table 104c. The main process of flaw detection is controlled by the CPU 102 according to the controlling program 104. The CPU 102 also executes the steps for processing the temperature profile data to the flaw profile data by subtracting the background from the temperature profile according to the data processing program 104b.

Figure 18A:
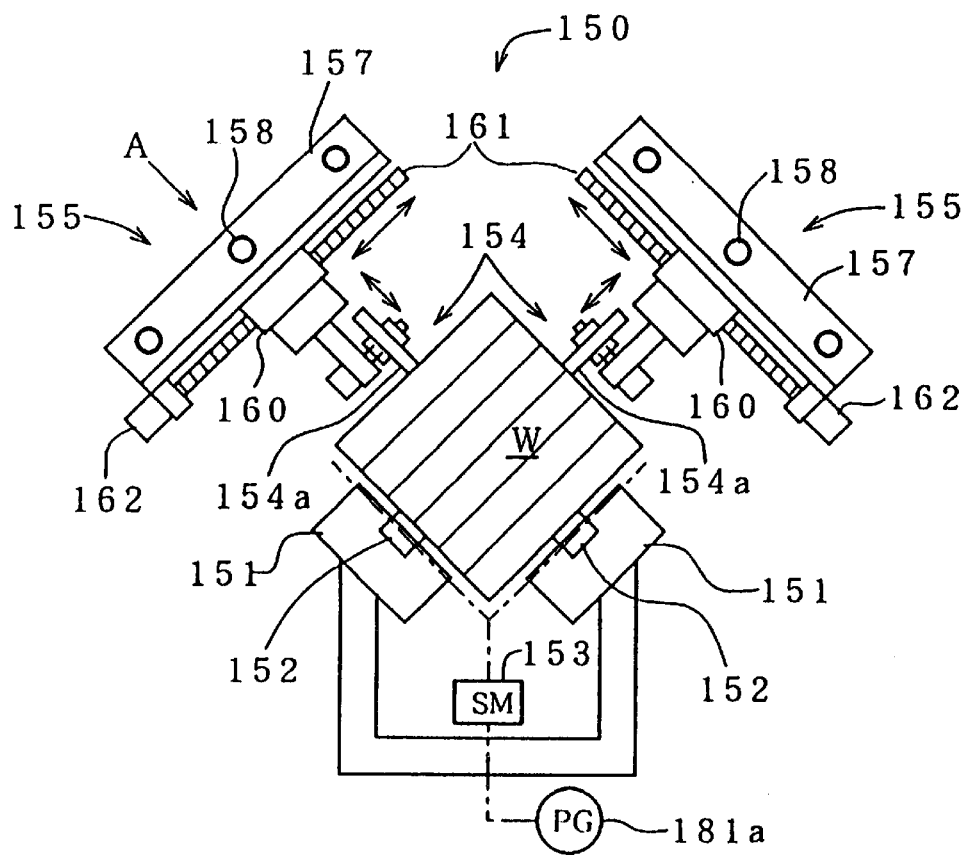
FIG. 18 is a figure of an embodiment of the flaw removing unit.
Figure 18B:
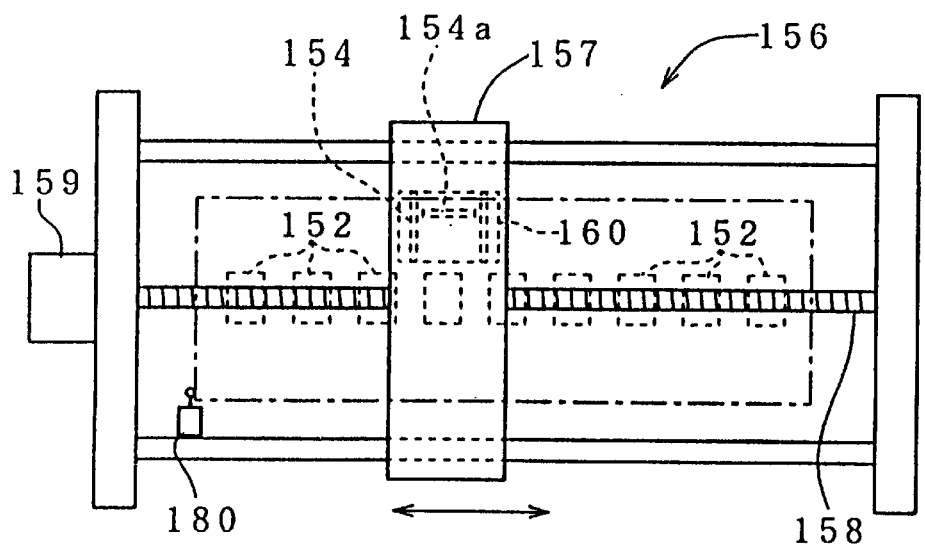

FIG. 18 shows one embodiment of flaw removing unit. The flaw removing unit 150 is arranged, for example, downstream of the coil 8 (or the powder removing device 11 in FIG. 1) on the member transportation passage. As shown in FIG. 18 (a), the member W is supported by the work supporting stand 151 from below. Plural guiding rollers 152 are rotatively mounted on each supporting surface of the frame 151 along the length of the member W, and cooperatively transport the member W being driven by a servo motor 153.

On the other hand, a grinder 154 as a flaw removing device and a grinder moving mechanism 155 (a flaw removing device moving mechanism) are arranged corresponding to each upper side surface of the member W supported by the frame 151. The grinder moving device 155 (moving mechanism) has a supporting frame 156. An X-moving base 157 is mounted on the supporting frame 156 movably in an X-direction set along the length of the member W. The X-moving base 157 moves forwardly or backwardly according to a bidirectional rotation of a threaded shaft 158 screwed through the base 157 by a servo motor 159. On the X-moving base 157, a Y-moving base 160 is mounted slidably in a Y-direction set along the width of the side surface of the member W. The Y-moving base is also driven by a mechanism comprising a threaded shaft 161 and servo motor 162 as well as the X-moving base 157. The grinder 154 is fixedly mounted on the Y-moving base 160 facing to the surface of the member W. The numeral 177 (FIG. 19) indicates a grinder infeed control mechanism which provides a designated infeed amount to the grinder wheel 154a by an unillustrated threaded shaft mechanism driven by a servo motor 177c (FIG. 19).

Figure 19:
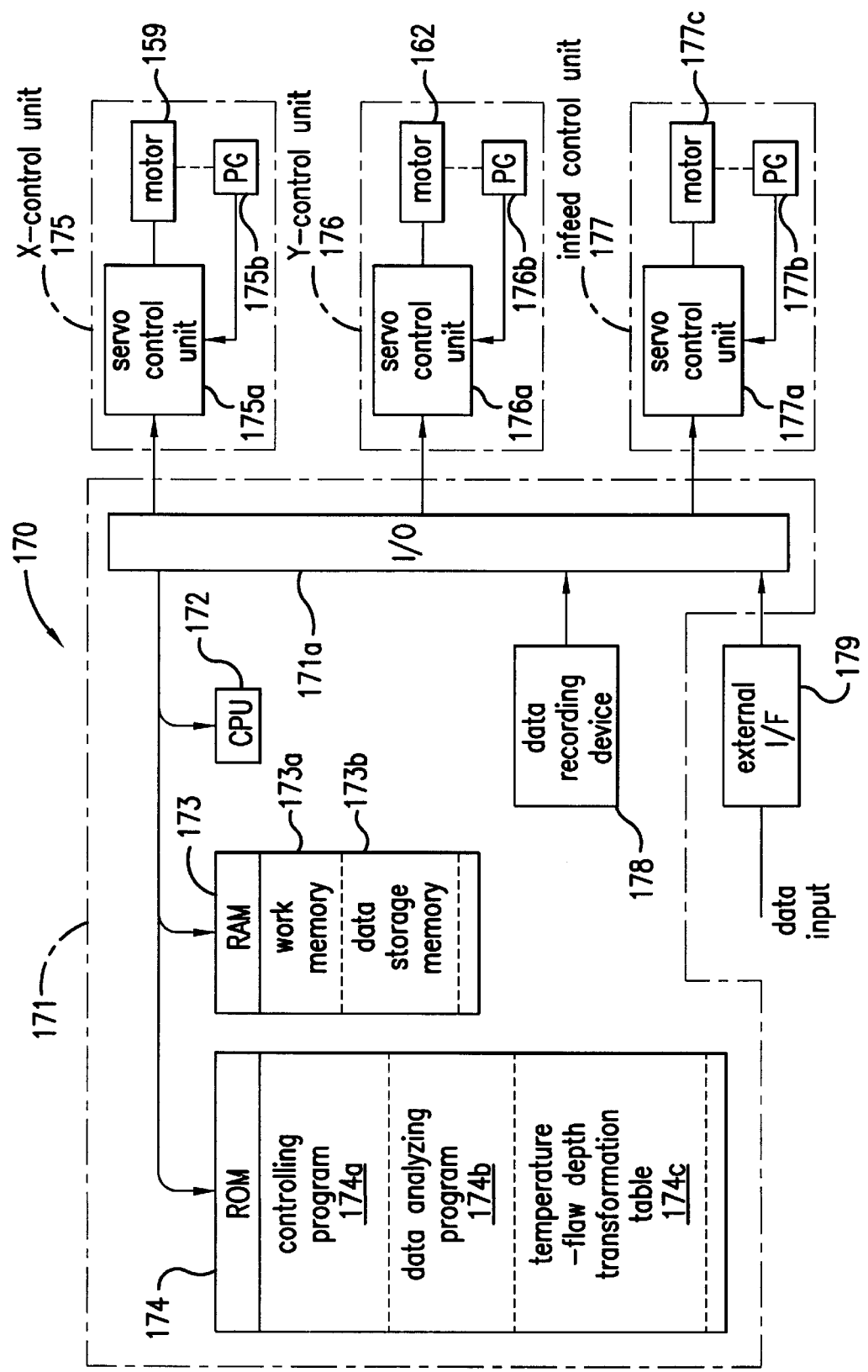
FIG. 19 is a block diagram of the control unit of the flaw removing unit.

FIG. 19 shows a block diagram of a control unit of the flaw removing unit 150. The control unit 170 comprises a micro processor 171 having an I/O port 171a, and CPU 172, RAM 173 and ROM 174 connected thereto. To the I/O port 171a, X-control unit 175, Y-control unit 176, infeed control unit 177, external interface 179, data recording device 178, such as a hard disk drive, are connected. CPU 172 functions as a flaw data generating means and a moving commander.

The X-control unit 175 has a servo control unit 175a to which the servo motor 159 and a pulse generator 175b for detecting the current X-position of the grinder wheel 154a are connected. The Y-control unit 176 has a servo control unit 176a to which the servo motor 162 and a pulse generator 176b for detecting the current Y-position of the grinder wheel 154a are connected. The infeed-control unit 177 has a servo control unit 177a to which the servo motor 177c for moving the grinder wheel 154a to and from the member W and a pulse generator 177b for detecting the current infeed amount of the grinder wheel 154a are connected.

In the RAM 173, a work memory 173a for the CPU 172 and a data storage memory 173b are formed. On the other hand, a controlling program 174a for controlling the operation of the flaw removing unit 150 is stored in the ROM 174. The main process of flaw removing is controlled by CPU 172 according to the controlling program 174a.

CPU 172 executes the steps of generating flaw data which includes data of flaw positions on the surface of the member W and flaw depths by using the flaw profile data sent from the controlling unit 100 in FIG. 17 according to the data analyzing program 174b. On the other hand in the table 174c in the ROM 174, data providing an experimentally-determined relationship between said temperature difference $\Delta T$ and flaw depth are stored. The CPU 172 generates the flaw depth data according to the value of $\Delta T$ corresponding to the flaw depth in the flaw profile data referring the table 174c.

Figure 20:
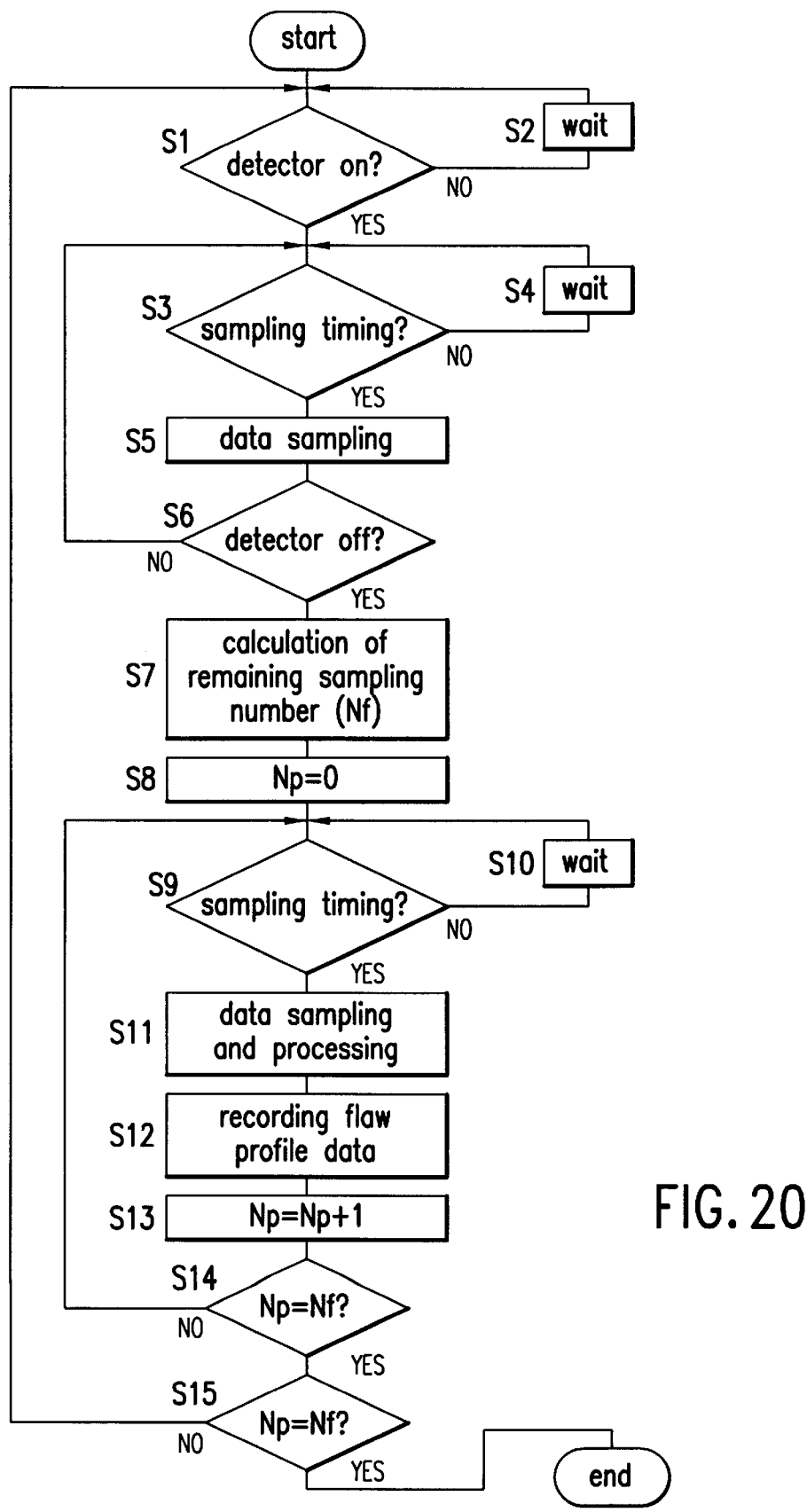
FIG. 20 is a flow chart of the flaw detection process.
Figure 21A:
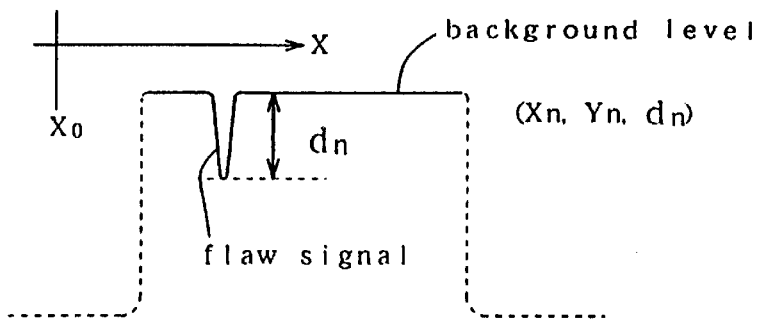
FIG. 21 is a figure explaining the process of flaw data.
Figure 21B:
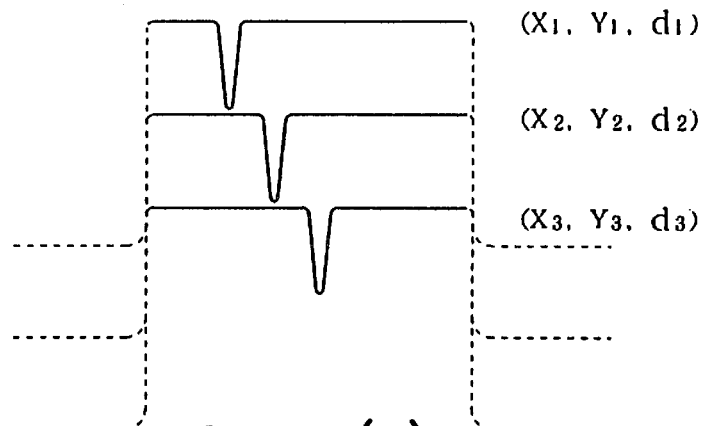
Figure 21C:
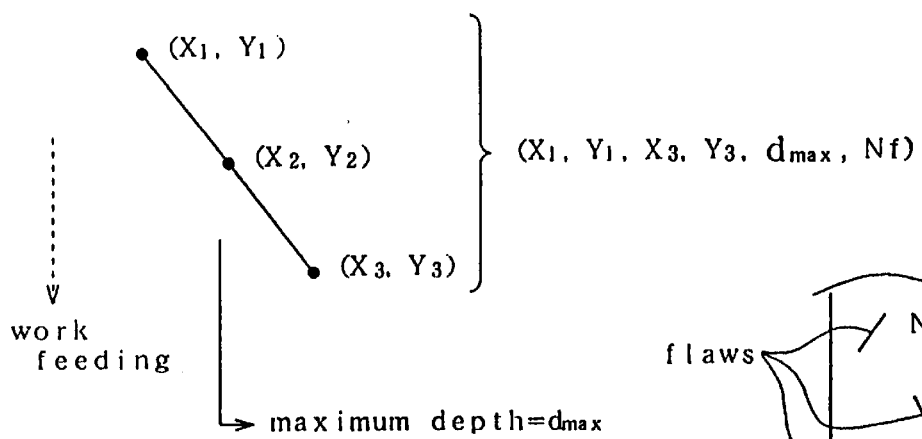
Figure 21D:
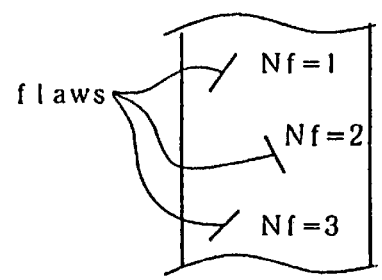

Now, the operation of flaw detecting apparatus 200 and the flaw removing unit 150 will be described on referring to FIG. 20 and FIG. 22. FIG. 20 presents a flow chart of the flaw detection process. When the member detector 112 (FIG. 16) detects the front end of the member W, the pulse of the PG 105 is started to be counted (S1). The distance between the member detector 212 and the coil 8 is fixed to Lk, so that the timing of the member arrival to the coil 8 can be determined according to the pulse number from the PG 105.

After the arrival of the member W to the coil, the sampling of the temperature profile is started (S3,S5). The radiation thermometer 9 is continuously detecting the temperature distribution, and the output thereof at the moment of sampling timing is digitized by the A/D converter 110a and taken by the micro processor 101 as a line-profile data of the temperature distribution along the width of the member as shown in FIG. 21. Plural sampling positions are equidistantly set along the length of the member W according to the sampling interval Ns (in the RAM 103) which is defined as a corresponding pulse number counted by PG 105.

The temperature profile obtained is processed into a flaw profile data and then recorded to the data recording device 108 (S12). FIG. 21 (a) presents a schematic example of a temperature profile. As described before, the normal (sound) part of the member W formes a background of constant temperature, and the flaw signal appears as a volley-like temperature peak on the background. The flaw profile can be extracted by subtracting the background level from the temperature profile according to the data processing program 104b. On the other hand, the X-coordinate of each point on the flaw profile is determined as the distance from a predetermined origin X0 along the X-direction. On the other hand, the Y-coordinate of each point on the flaw profile can be determined according to the total pulse number from PG 105 up to the corresponding sampling timing from the first profile sampling. The flaw profile data is thus recorded as a set of data points (X, Y, ΔT) wherein X and Y are the X- and Y-coordinates of the data point, and ΔT is the absolute value of the background-subtracted temperature signal.

The member detector 112 finishes work detection when the back end of the member W arrives thereto. At this moment however, the part of the member W between the detector 112 and the coil 8 (with the length Lk) is remaining without being inspected, so that the data sampling is continued until the back end of the member W arrives to the coil 8. The remaining number of the data sampling times can be determined as Lk/(Ns.da), wherein da is a member transportation amount corresponding to one pulse interval. Then, the data sampling is finished (S7–S14).

Figure 22:
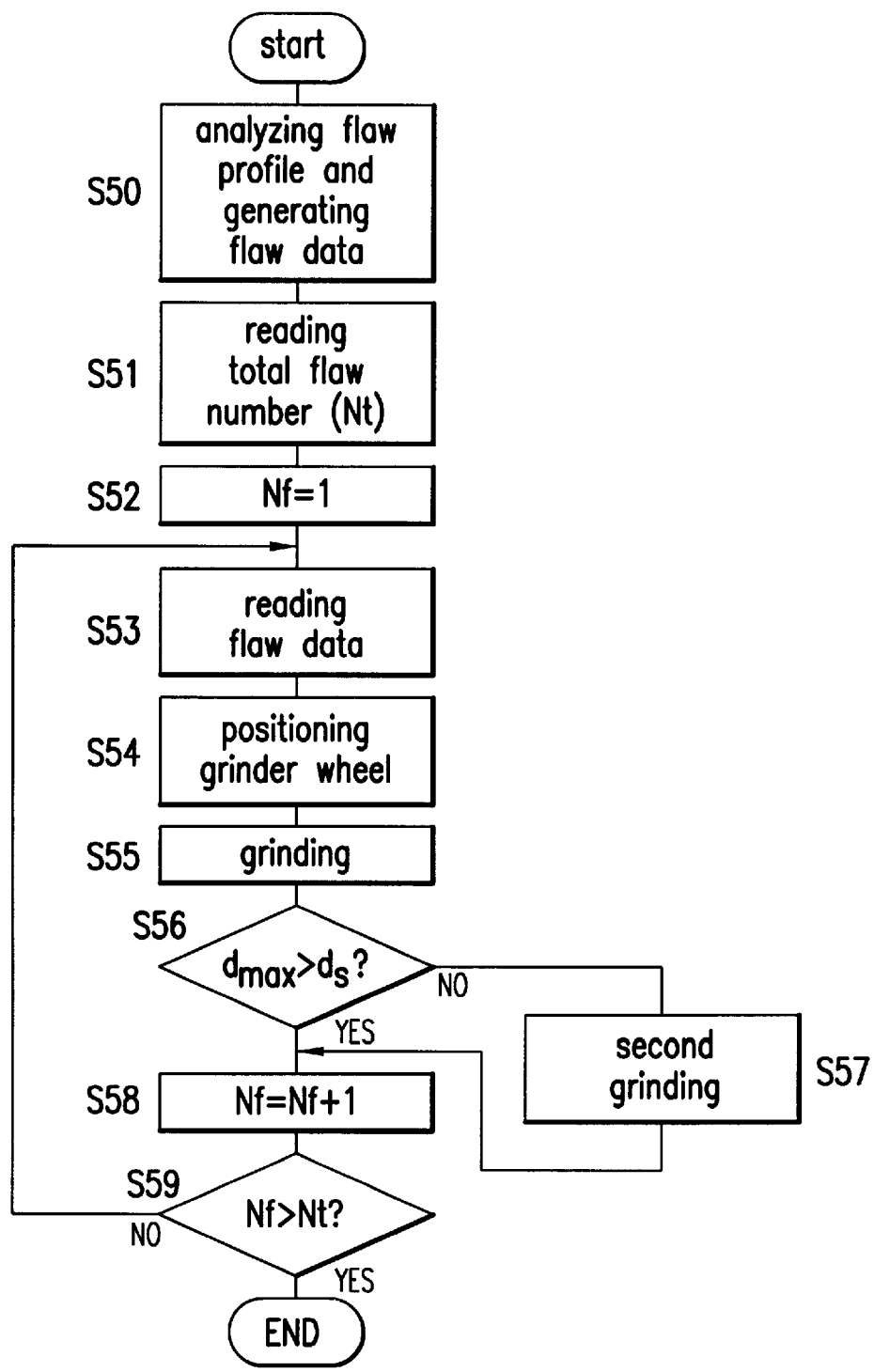
FIG. 22 is a flow chart of the flaw removing process.

FIG. 22 presents a flow chart of the flaw removing process. As shown in FIG. 18, the member W after the flaw detection is transported into the flaw removing unit 150. When the front end of the member W activates the sensor 180, such as a limit switch or a proximity switch, the motor 153 for driving the guiding rollers 152 is slowed down and stopped when a designated number of pulses from PG 181a (connected to the motor 153) is detected after the activation of the sensor 180, thereby positioning the member W in the flaw removing unit 150.

On the other hand, the flaw profile data is read from the data recording device 108 of the controlling unit 100 and transferred to the I/O port 171a of the flaw detecting unit 150 (FIG. 19) through external interfaces 109 and 179. In the step of S50, flaw data which specifies each flaw detected on the member is generated according to an analysis on the flaw profile data. Each flaw profile data provides information regarding the cross sectional configuration of a flaw, so that as shown in FIG. 21 (b), the detailed configuration of each flaw can be described by a series of flaw profiles taken over the member surface area covering the whole part of the flaw. As shown in FIG. 21 (a) and (b), the coordinates of both end points of each flaw, (X1,Y1) and (X3,Y3), and the maximum value of ΔT (ΔTmax), i.e., the peak depth of the flaw signal, can be determined on referring to the series of the flaw profiles. ΔTmax is transformed into a value of the maximum flaw depth dmax according to the transformation table 104c. Then, the flaw data is generated as a set of values of parameters (X1, X2, Y1, Y2, dmax: Nf), wherein Nf is a serial number of each flaw, and recorded in the data recording device 108.

Figure 23A:
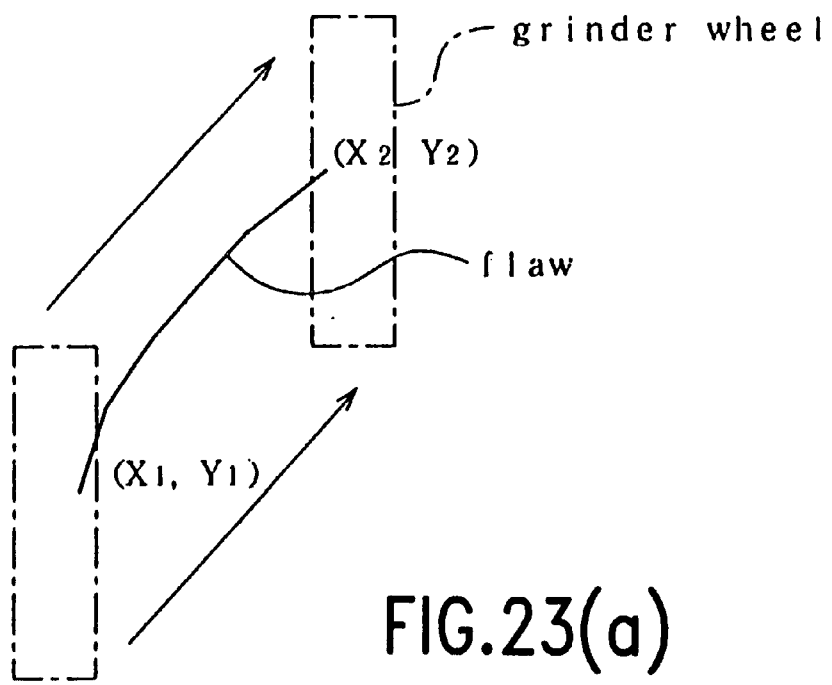
FIG. 23 is a figure explaining the grinding process.
Figure 23B:
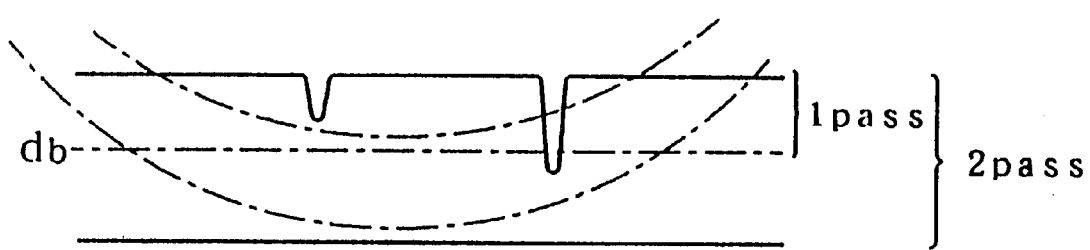

In the step of S51 in FIG. 22, total number N+ of the flaws is determined according to the serial number Nf of the flaws. Then, the data of the first flaw is read, and grinder 154 is moved by the X- and Y-control units 175 and 176 and is located to the starting end point (X1,Y1) of the flaw, as shown in FIG. 23 (a) (S53 and S54). After that, the grinder 154 moves toward the finishing end point (X3,Y3) along the flaw with grinding the surface of the member W at a designated infeed amount. As shown in FIG. 23 (b), if the maximum depth dmax of the flaw is larger than a designated reference value db, the grinder 154 moves back to the starting end point (X1,Y1) for secondary grinding in order to remove sufficiently the flaw by a 2-pass grinding. If not, the secondary grinding is not performed (1-pass grinding) (S55–S57). The steps S53–S57 is repeated for all flaws.

Figure 29:
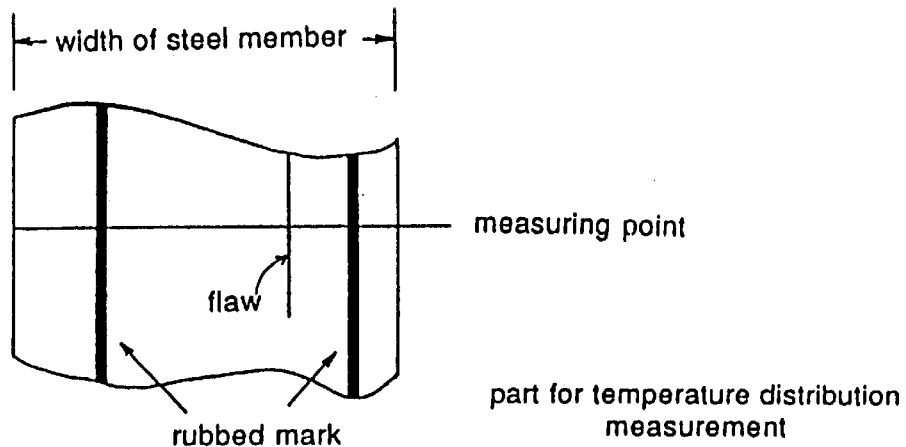
FIG. 29 is a figure explaining the surface state of the member.

Now, it will be described about the case that the induction heating flaw detection method of this invention is applied to a member having a surface condition as shown in FIG. 29. For a comparative example the member shown in FIG. 29 is subjected to a flaw detection by means of a conventional flaw detection method, and the result is presented in FIG. 30 (a). As it is clear from FIG. 30 (a), the parts of rubbed marks (handling marks) exhibit low temperature as well as the flaw part so that it is difficult to distinguish the flaw and the rubbed marks.

For an example of this invention surface of the member shown in FIG. 29 was covered with powder particles with 40 μm of average diameter. The rate of powder spraying was 50 m/min, and the average thickness of the powder layer t0 formed was 20 μm. The average thickness was measured in the following method. After finishing the flaw detection, the powder was removed from the surface of the member, and the removed powder was gathered and weighed. By using real density of the powder, ρ, total powder weight, W1, and coverage area, Sc, the average thickness t0 can be obtained as;

$$t0 = W1/(\rho \times Sc) \tag{5}$$

Figure 30A:
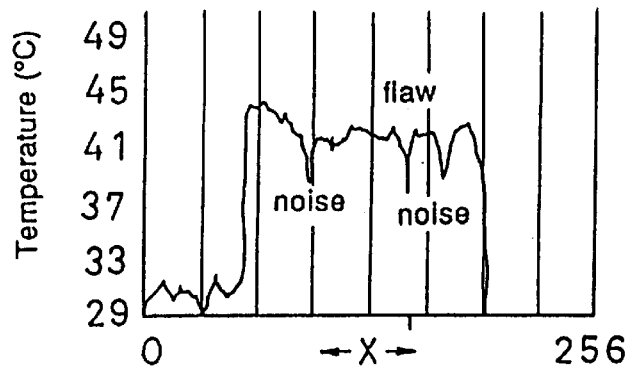
FIG. 30 is a graph showing the result of the flaw detection.
Figure 30B:
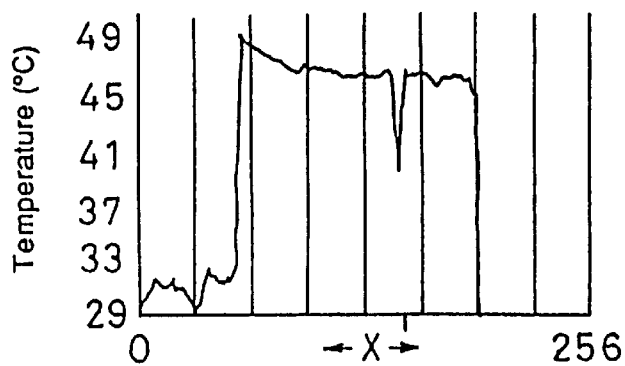

The result of the flaw detection for this member is presented in FIG. 30 (b). FIG. 30 (b) shows that only the flaw part is detected as a low temperature part.

Figure 24:
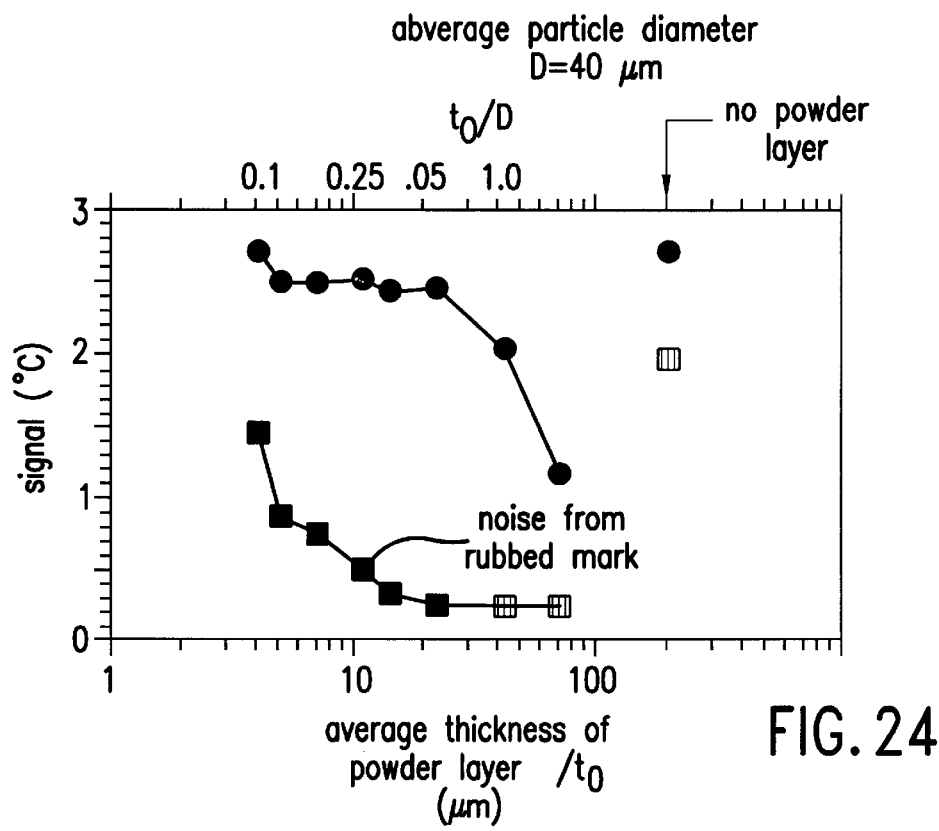
FIG. 24 is a figure presenting the relationship between the flaw signal and the average thickness of the powder layer.

The experiment mentioned above was repeatedly performed with varying the average thickness t0 of the powder layer in the same procedure, and the levels of the real flaw signal and that of the false signal from the rubbed mark were measured, respectively. The results are presented in FIG. 24. When t0 becomes less than 0.1D, the noise signal level seems to increase drastically. On the other hand, when t0 exceeds 0.6D, the flaw signal level significantly decreases.

Figure 25:
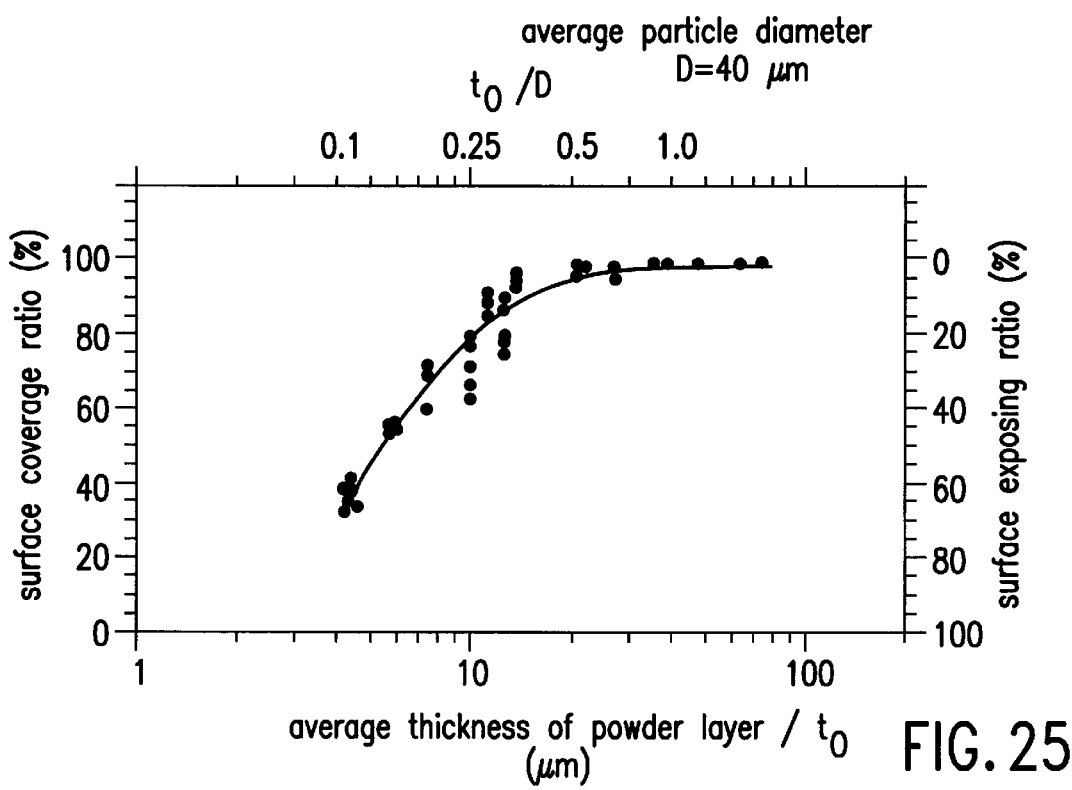
FIG. 25 is a figure presenting the relationship between the average thickness of the powder layer and the surface exposing ratio.
Figure 26A:
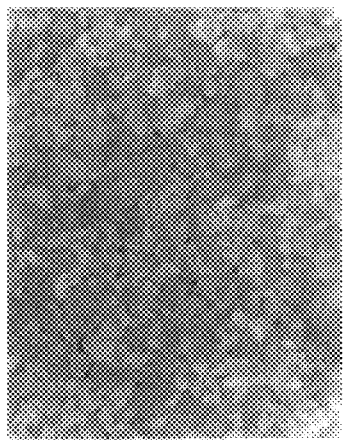
FIG. 26 are examples of SEM image of the member surface covered with the powder layer.
Figure 26B:
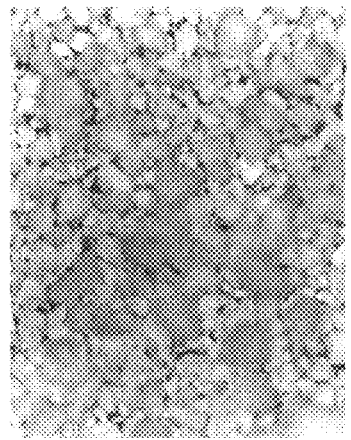
Figure 26C:
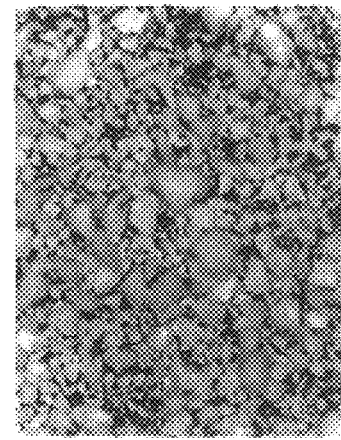
Figure 26D:
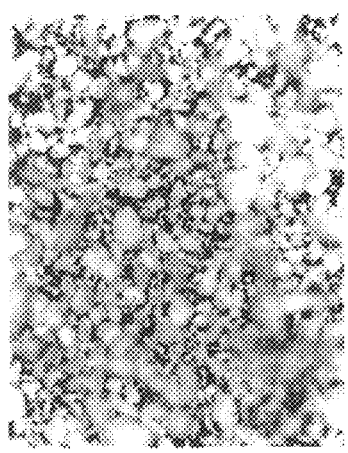
Figure 26E:
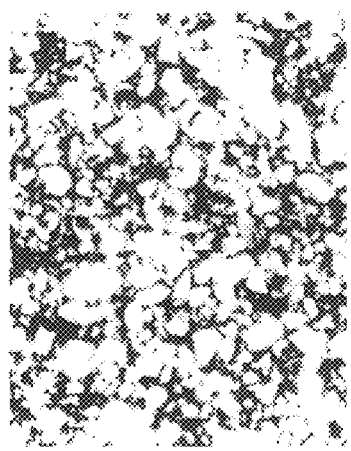
Figure 26F:
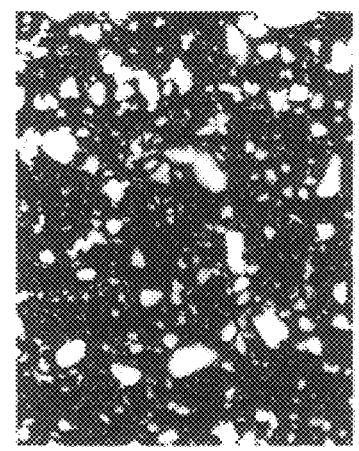

Furthermore, the member surface covered with the powder layer was observed by using a scanning electron microscopy (SEM) for each conditions of the average thickness of the powder coverage. The surface exposing ratio was measured by performing a publicly known digital picture processing method for the SEM photograph taken for each condition. FIG. 25 presents the relationship between the average thickness of the powder layer and the surface exposing ratio. This shows that the critical range of to (0.1D–0.6D) approximately corresponds to the range of the surface exposing ratio of 2–70%.

FIG. 26 presents several examples of SEM images. In each image, the exposed part is appeared as a black area. FIG. 26 (a) corresponds to the condition of t0=0.88D (exposing ratio is 0.1%). FIG. 26 (b) corresponds to the condition of t0=0.5D (exposing ratio is 2.8%). FIG. 26 (c) corresponds to the condition of t0=0.28D (exposing ratio is 12.4%). FIG. 26 (d) corresponds to the condition of t0=0.25D (exposing ratio is 20%). FIG. 26 (e) corresponds to the condition of t0=0.19D (exposing ratio is 31.7%). FIG. 26 (f) corresponds to the condition of t0=0.1D (exposing ratio is 63.6%).

What is claimed is:

1. A method for detecting flaws on a surface of a member to be inspected comprising the steps of:

forming a powder layer on said surface of said member by depositing dry powder thereon so that said surface is partly exposed, heating the surface region of said member by high frequency induction heating;

measuring the temperature distribution on said surface of the heated member covered with said powder layer according to the energy emission from said surface of the member by a radiation thermometer;

detecting the flaws on said member according to said temperature distribution on said surface of said member; and removing said powder layer and determining the average thickness of said powder layer after removal of the powder, said average thickness being between 0.1D–0.6D, where D is an average powder particle diameter under an assumption that the powder particles in said powder layer are dispersed into a uniform thickness film.

2. The method according to claim 1 wherein said average thickness of said powder layer is 0.25D–0.5D.

3. A method for detecting flaws on a surface of a member to be inspected comprising the steps of:

forming a powder layer on said surface of said member by depositing dry powder thereon so that said surface is partly exposed with a surface exposing ratio 2–70%;

heating the surface of said member by a high frequency induction heating;

measuring a temperature distribution on said surface of the heated member covered with said powder layer according to an energy emission from said surface of the member by a radiation thermometer; and detecting the flaws on said member according to said temperature distribution on said surface of said member.

4. The method according to claim 3 wherein the average thickness of said powder layer is 0.1D–0.6D, where D is the average particle diameter of said powder, under an assumption that the powder particles are virtually leveled into a uniform thickness film.

5. The method according to claim 3 wherein said surface exposing ratio is 5–40%.

6. The method according to claim 5, wherein said powder layer on said surface of said member has an average thickness of said powder layer of 0.25D–0.5D.

7. An apparatus for detecting flaws on a surface of a member comprising:

a transportation line for transporting said member to be inspected;

a powder deposition device mounted on said transportation line and configured to form a powder layer on said surface of said member by depositing dry powder thereon so that said surface is partly exposed by setting an average thickness of said powder layer to 0.1D–0.6D, where D is an average particle diameter of said powder, under an assumption that the powder particles in said powder layer are dispersed into a uniform thickness film;

a high frequency induction heating device mounted on said transportation line for heating the surface of said member;

a radiation thermometer for measuring a temperature distribution on said surface of the heated member covered with said powder; and a detecting device for detecting said flaws on said member according to said temperature distribution.

8. The apparatus according to claim 7 wherein said high frequency induction heating device comprises a heating coil having a cavity into which said member is inserted, and wherein the Lc/Dcmax is less than ½, where Lc is the coil length and Dcmax is the maximum cross sectional dimension of said cavity.

9. The apparatus according to claim 8 wherein said heating coil has an aperture formed through the wall thereof from inside to outside, and wherein said radiation thermometer measures the temperature distribution on said surface of the member in said heating coil through said aperture.

10. The apparatus according to claim 8 wherein said radiation thermometer measures the temperature distribution on said surface of the member in said heating coil from an inclined direction through a gap between said heating coil and said member inserted thereinto.

11. The apparatus according to claim 7 wherein said radiation thermometer detects the temperature distribution on said surface of said member in transportation along a predetermined detecting line set in a direction crossing with a transportation direction of said member further comprising:

a temperature distribution data generating means which performs the sampling of the output from said radiation thermometer at a designated sampling timing, thereby generating sets of temperature distribution profile data along said detecting line at a position determined on the surface of said member corresponding to said sampling timing;

a sampling commander which commands said temperature distribution data generating means to perform said sampling at a designated time interval corresponding to a transportation speed of said member so that said temperature distribution data generating means generates said sets of said temperature profile data which correspond to different positions on said surface of said member in said transportation direction; and a flaw data generating means which generates flaw data at least for specifying the position of said flaws on said surface of said member according to said sets of temperature profile data.

12. The apparatus according to claim 11 further comprising:

a flaw removing device which is movable along said surface of said member and removes a flaw existing on said surface;

a moving mechanism which moves said flaw removing device independently in two or more directions crossing each other so as to be able to position said flaw removing device at a flaw site on said surface of said member;

a moving commander which commands said moving mechanism to move said flaw removing device to a flaw site determined according to a flaw data.

13. The apparatus according to claim 12 comprising a member supporting means for supporting said member so as to be fixedly positioned in a designated site;

wherein said flaw removing device removes said flaws on said member supported by said member supporting means.

14. The apparatus according to claim 7;

wherein a bar-like member with a square-like axial cross section is used as said member to be inspected;

wherein said bar-like member is transported in the longitudinal direction thereof so that one diagonal line of said square-like axial cross section is almost vertically directed;

wherein said transportation line comprises a pair of member transportation rollers which pinches said member from above and below, respectively, and whose roller surface has a V-shaped cross section corresponding to the corner shape of said square-like axial cross section of said member.

15. An apparatus for detecting flaws on a surface of a member to be inspected comprising:

a transportation line for transporting said member to be inspected;

a powder deposition device mounted on said transportation line and configured to form a powder layer on said surface of said member by depositing dry powder thereon so that said surface is partly exposed with an surface exposing ratio of 2–70%;

a high frequency induction heating device mounted on said transportation line for heating the surface of said member;

a radiation thermometer for measuring the temperature distribution on said surface of the heated member covered with said powder; and a detecting device for detecting flaws on said member according to said temperature distribution.

* * * * *